(12) United States Patent
    Ariyoshi

(10) Patent No.: US 9,074,971 B2
(45) Date of Patent: Jul. 7, 2015

(54) SAMPLE PROCESSING APPARATUS AND NON-TRANSITORY STORAGE MEDIUM

(75) Inventor: Shunsuke Ariyoshi, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 764 days.

(21) Appl. No.: 13/282,152

(22) Filed: Oct. 26, 2011

(65) Prior Publication Data

US 2012/0109529 A1    May 3, 2012

(30) Foreign Application Priority Data

Oct. 29, 2010 (JP) .................. 2010-243033

(51) Int. Cl.
    *G01N 1/31* (2006.01)
    *G01N 35/00* (2006.01)
    *G01N 35/02* (2006.01)

(52) U.S. Cl.
    CPC .......... *G01N 1/312* (2013.01); *G01N 35/00722* (2013.01); *G01N 35/026* (2013.01); *G01N 2035/0091* (2013.01)

(58) Field of Classification Search
    CPC ......... G06F 19/10; G06F 19/266; G06F 7/00; G01N 1/312; G01N 35/026; G01N 35/007; G01N 2035/0091
    USPC ....................................... 702/127
    See application file for complete search history.

(56) References Cited

U.S. PATENT DOCUMENTS

| 7,565,628 B2 * | 7/2009 | Kim et al. ................. 715/856 |
| 2007/0078631 A1 * | 4/2007 | Ariyoshi et al. ............. 702/189 |
| 2010/0101339 A1 * | 4/2010 | Tatsutani et al. ........... 73/863.91 |

FOREIGN PATENT DOCUMENTS

| JP | 10-038889 A | 2/1998 |
| JP | 2009058352 A | 3/2009 |
| JP | 2009-250657 | 10/2009 |

* cited by examiner

*Primary Examiner* — John Breene
*Assistant Examiner* — Lynda Dinh
(74) *Attorney, Agent, or Firm* — Sughrue Mion, PLLC

(57) ABSTRACT

A sample processing apparatus includes: a first sample processing unit; a second sample processing unit; and a data processing unit connected to the first and the second sample processing units. The data processing unit includes: a display device; an input device; and a controller configured to show a screen image on the display device, wherein the screen image comprises a shared region which is shared for displaying information of each of the first and the second sample processing units, a first operation section operable by a user to control the first sample processing unit and a second operation section operable by the user to control the second sample processing unit, and control the first sample processing unit in response to an operation of the first operation section, and control the second sample processing unit in response to an operation of the second operation section.

18 Claims, 15 Drawing Sheets ly, the Japanese Laid-Open Patent Publication No. 10-38889 discloses an automatic analysis apparatus

SAMPLE PROCESSING APPARATUS AND NON-TRANSITORY STORAGE MEDIUM

FIELD OF THE INVENTION

The present invention relates to a sample processing apparatus and a non-transitory storage medium used for sample measurement and sample processes such as production of a smear sample.

BACKGROUND

A conventional sample processing apparatus includes a plurality of sample processing units and a display device connected to the sample processing units (see Japanese Laid-Open Patent Publication No. 10-38889).

More specifically, the Japanese Laid-Open Patent Publication No. 10-38889 discloses an automatic analysis apparatus provided with two analyzers and a display device configured to display an operation screen of the analyzers. The automatic analysis apparatus displays on the display device, for example, a screen showing a list/summary table of measured data as an operation screen of the two analyzers, which is shared by the two analyzers. When a maintenance screen of the analyzers is displayed in the automatic analysis apparatus, a window frame of the display device is divided into two display regions. A maintenance screen of one of the analyzers is displayed on one of the display regions, while a maintenance screen of the other analyzer is displayed on the other display region. A photometer check button, for example, is displayed on the maintenance screen, and when a user selects the photometer check button, a photometer check can be carried out as a maintenance operation of the analyzer.

In the Japanese Laid-Open Patent Publication No. 10-38889, however, the maintenance screens for the two analyzers cannot be displayed on the display device while the list/summary table screen shared by the two analyzers is being displayed. This demands the user to cancel the currently displayed list/summary table screen before displaying the maintenance screens of the analyzers when he wants to carry out the maintenance of the analyzers while the list/summary table screen is still displayed, which is rather troublesome for the user.

SUMMARY

The scope of the present invention is defined solely by the appended claims, and is not affected to any degree by the statements within this summary.

A first aspect of the present invention is a sample processing apparatus, comprising: a first sample processing unit configured to process a sample; a second sample processing unit configured to process a sample; and a data processing unit connected to the first and the second sample processing units so as to communicate therewith. The data processing unit includes: a display device; an input device; and a controller configured to show a screen image on the display device, wherein the screen image comprises a shared region which is shared for displaying information of each of the first and the second sample processing units, a first operation section operable through the input device by a user to control the first sample processing unit and a second operation section operable through the input device by the user to control the second sample processing unit, and control the first sample processing unit in response to an operation of the first operation section by the user, and control the second sample processing unit in response to an operation of the second operation section by the user.

A second aspect of the present invention is at least one non-transitory storage medium which stores programs executable collectively by at least one processor to: show a screen image on a display device, wherein the screen image comprises a shared region which is shared for displaying information of each of a first sample processing unit and a second sample processing unit, a first operation section operable by a user to control the first sample processing unit and a second operation section operable by the user to control the second sample processing unit; and control the first sample processing unit in response to an operation of the first operation section, and control the second sample processing unit in response to an operation of the second operation section.

DETAILED DESCRIPTION OF THE EMBODIMENT

Hereinafter, preferred embodiments of the present invention are described in detail referring to the accompanied drawings.

[Configuration of Sample Processing System]

Figure 1:
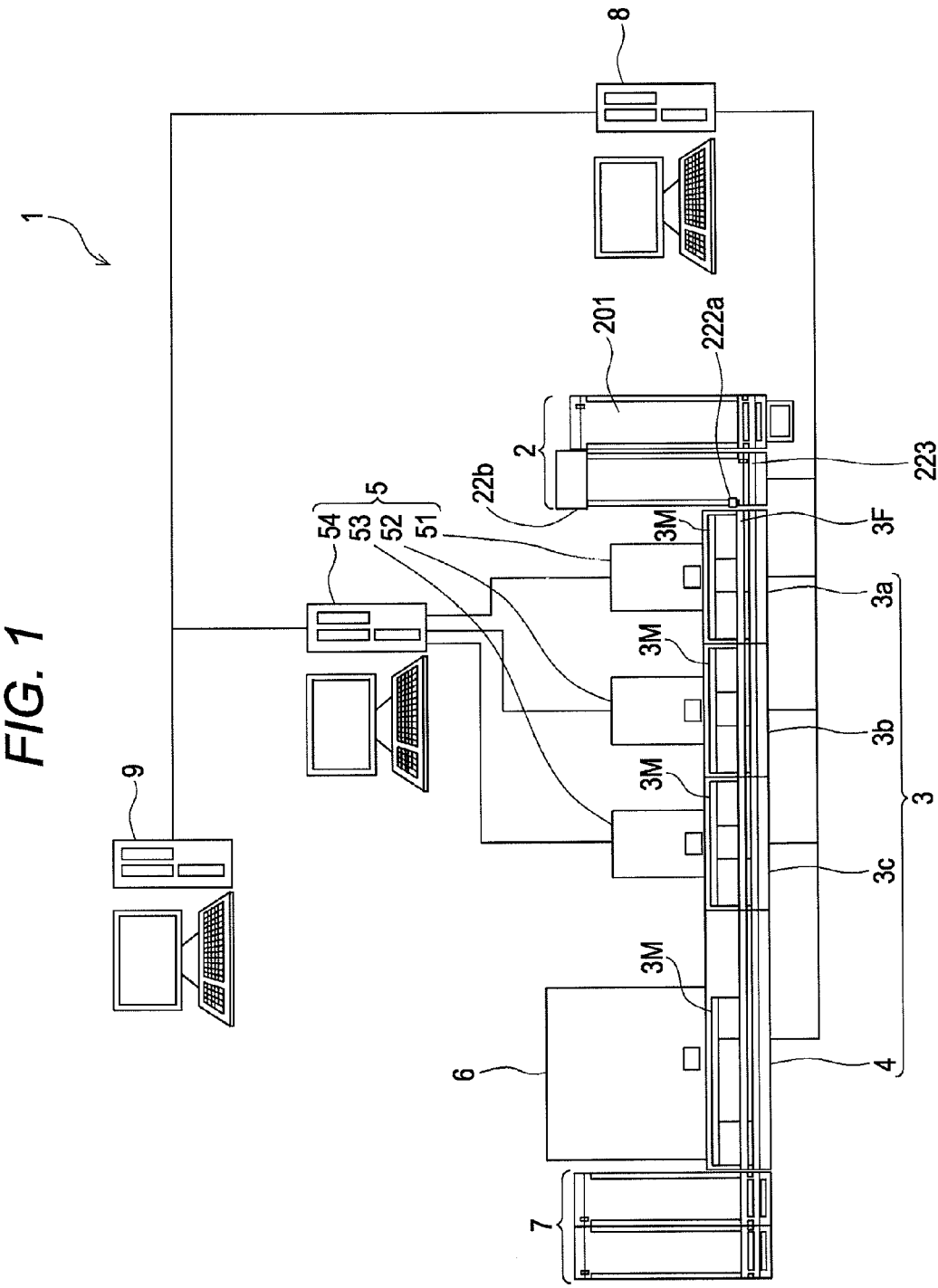
FIG. 1 is a schematic plan view illustrating an overall structure of a sample processing system according to an embodiment of the present invention.

FIG. 1 is a schematic plan view illustrating an overall structure of a sample processing system according to an embodiment of the present invention. Referring to FIG. 1, the sample processing system 1 includes a sample dispatch apparatus 2, a sample transport apparatus 3, a blood cell analysis apparatus 5, a smear sample production apparatus 6, a sample recovery apparatus 7, and a system control apparatus 8. The sample processing system 1 according to the exemplary embodiment is connected to a test information management apparatus 9 through a communication network to allow communication therebetween.

The sample transport apparatus 3 includes sample transport units 3a, 3b, 3c, and 4. The sample transport units 3a, 3b, 3c, and 4 are serially connected to one another in an aligned manner laterally on the drawing. The blood cell analysis apparatus 5 includes three measurement units 51, 52, and 53 and an information processing unit 54. The measurement unit 51 is provided behind the sample transport unit 3a, the measurement unit 52 is provided behind the sample transport unit 3b, and the measurement unit 53 is provided behind the sample transport unit 3c. The smear sample production apparatus 6 is provided behind the sample transport unit 4.

In the sample processing system 1, a sample rack holding a plurality of sample containers is set by a user in a rack setting section 201 of the sample dispatch apparatus 2. A barcode label showing a sample ID is printed on a side surface of each sample container, and a barcode label showing a rack ID is attached to a side surface of the sample rack. The sample rack set in the rack setting section 201 is transported from a rack dispatch position 223 to a transport line 3F of the sample transport apparatus 3 by way of barcode readers 22b and 222a. The measurement unit to which the sample rack is transported is decided based on the sample IDs and the rack ID read by the barcode readers 22b and 222a.

The sample rack transported to the transport line 3F is then transported leftward in the drawing. The sample transport apparatus 3 is provided with the transport line 3F and a measurement line 3M, so that the sample rack is transported to and from the transport line 3F and the measurement line 3M. The sample rack which departed from the sample dispatch apparatus 2 is transported by the transport line 3F and the measurement line 3M to the measurement unit decided as its destination.

After the samples are supplied to the measurement units 51-53 or the smear sample production apparatus 6, the sample rack is transported leftward by the transport line 3F and then recovered by the sample recovery apparatus 7.

[Configuration of Blood Cell Analysis Apparatus 5]

The blood cell analysis apparatus 5 is a multichannel blood cell analysis apparatus in which optical flow cytometry is employed. The blood cell analysis apparatus 5 obtains, for example, side scattered light intensity and fluorescence intensity of blood cells included in a blood sample, and classifies the blood cells included in the sample into different categories based on the obtained information and then counts the blood cells by each category. The blood cell analysis apparatus 5 creates and displays a scattergram in which the blood cells thus classified into different categories are respectively shown in different colors. The blood cell analysis apparatus 5 includes measurement units 51, 52, and 53 which respectively measure blood samples, and an information processing unit 54 including a computer configured to process measured data outputted from the measurement units 51, 52, and 53 and display analysis results of the respective blood samples.

As illustrated in FIG. 1, the blood cell analysis apparatus 5 includes three measurement units 51, 52, and 53, and an information processing unit 54. The information processing unit 54 is connected to three measurement units 51, 52, and 53 so as to communicate with the measurement units 51, 52, and 53 and control the operations of these three measurement units. The information processing unit 54 is also connected to three sample transport units 3a, 3b, and 3c respectively provided in front of three measurement units 51, 52, and 53 so as to communicate with these sample transport units.

Figure 2:
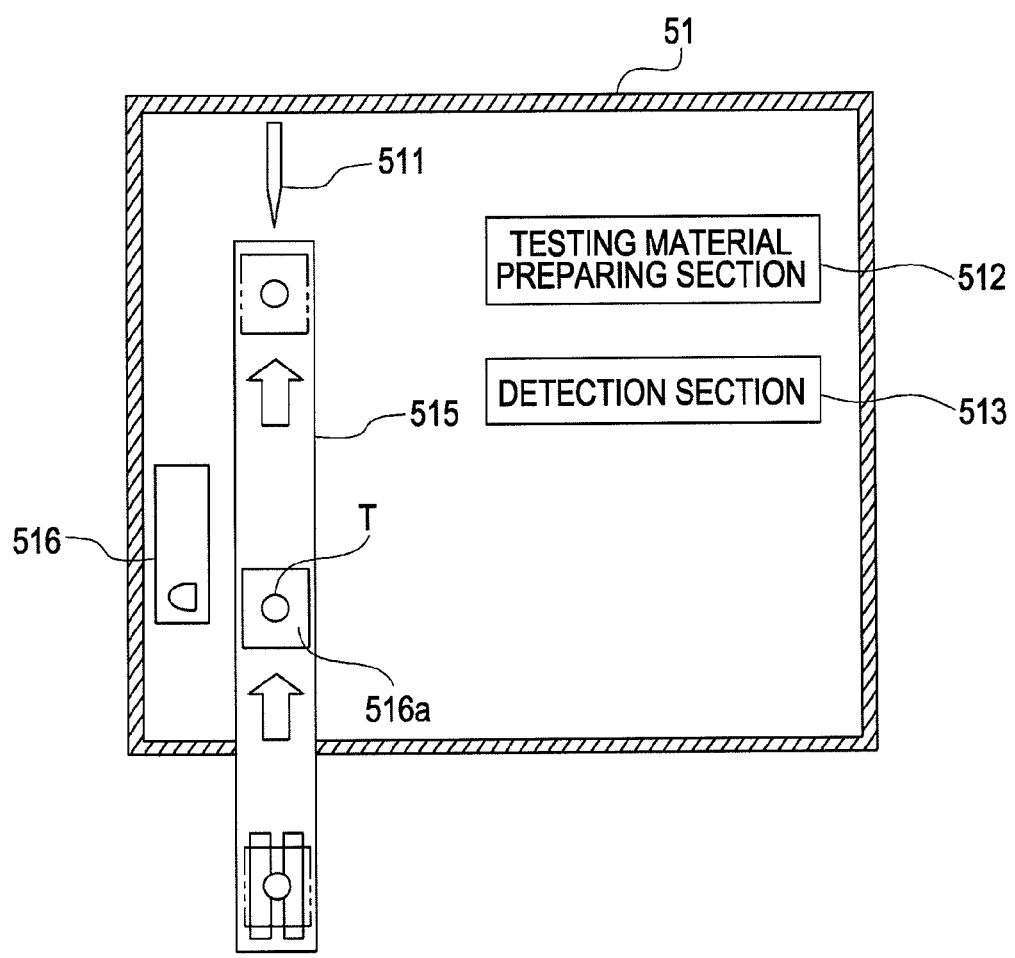
FIG. 2 is a block diagram illustrating a structure of a measurement unit provided in a blood cell analysis apparatus according to the embodiment.

FIG. 2 is a block diagram illustrating a structure of the measurement unit 51. Referring to FIG. 2, the measurement unit 51 has a sample suctioning section 511 which suctions blood collected as a sample from a sample container (blood collection tube) T, a testing material preparing section 512 which prepares a testing material for measurement from the blood suctioned by the sample suctioning section 511, and a detection section 513 which detects blood cells from the testing material for measurement prepared by the testing material preparing section 512. Further, the measurement unit 51 has a fetching port (not illustrated in the drawing) through which the sample container held in the sample rack transported by the measurement line 3M of the sample transport unit 3a is fetched into the measurement unit 51, a sample container transport section 515 which fetches the sample container from the sample rack into the measurement unit 51 and transports the fetched sample container to a suctioning position where the sample is suctioned by the sample suctioning section 511, and a barcode reader 516 which reads the sample ID from the barcode of the sample container fetched into the measurement unit 51.

The testing material preparing section 512 has a plurality of mixing chambers. The sample suctioning section 511 suctions a predetermined quantity of whole blood sample from the sample container using a syringe pump (not illustrated in the drawing), and distributes the predetermined quantity of whole blood sample into the chambers using the syringe pump. To the testing material preparing section 512 is connected a plurality of reagent containers containing therein various reagents such as diluent, coloring reagent and hemolytic agent for measuring NRBC (nucleated red blood cell), and coloring reagent and hemolytic agent for measuring DIFF (differential leukocyte count). The reagent is supplied from the reagent container to the mixing chamber and mixed with the sample and agitated in the mixing chamber so that the testing material for measurement used for the sample measurement is prepared.

The detection section 513 can detect RBC (red blood cells) and PLT (platelets) by employing sheath flow DC detection. The detection section 513 can detect HGB (hemoglobin) by employing SLS-hemoglobin, and WBC (white blood cells) by employing flow cytometry in which semiconductor laser is used. The measurement items, RBC, PLT, HGB, and WBC, are included in discrete item "CBC". When a measurement order requesting CBC measurement is inputted, the sample measurement is performed for RBC, PLT, HGB, and WBC. The discrete item is selected when the user requests the apparatus to measure a plurality of measurement items at a time.

The detection section 513 can measure leukocyte categories (discrete item, "DIFF") by employing flow cytometry in which semiconductor laser is used. In the measurement of leukocyte categories, a reagent for leukocyte categories is mixed with a sample, and a mixed solution thus obtained, which is a testing material, is supplied to a flow cytometer to detect optical information (side scattered light, forward scattered light, fluorescent light) generated when light is irradiated on blood cells included in the testing material. The optical information is outputted to the information processing unit 54. The information processing unit 54 processes the inputted optical information to thereby divide white blood cells in the sample into five subclasses (neutrophil (NEUT), lymphocyte (LYMPH), eosinocyte (EO), basocyte (BASO), and monocyte (MONO)), and counts the blood cells of each subclass. When a measurement order requesting DIFF measurement is inputted, the sample measurement is performed for each item of NEUT, LYMPH, EO, BASO, and MONO.

Similarly to the measurement unit 51, the measurement unit 52 has a sample suctioning section, a testing material preparing section, a detection section, and a sample container transport section.

The measurement unit 53 can measure RET (reticulocyte) other than CBC and DIFF by employing flow cytometry in which semiconductor laser is used. Other than capable of measuring RET, the measurement unit 53 is configured similarly to the measurement unit 51, including a sample suctioning section, a testing material preparing section, a detection section, and a sample container transport section.

There are two measurement modes that can be set in the measurement units 51, 52, 53 to be operational, which are; a sampler measurement mode in which the sample container is fetched from the sample rack automatically transported by the sample transport apparatus 3 to measure the sample contained in the fetched sample container, and a manual measurement mode in which the sample container placed in the sample container transport section 515 is manually fetched by the user to measure the sample contained in the fetched sample container. When the user presses a mode setting switch (not illustrated in the drawing) provided in each of the measurement units 51, 52 and 53, one of the measurement modes is set.

Figure 3:
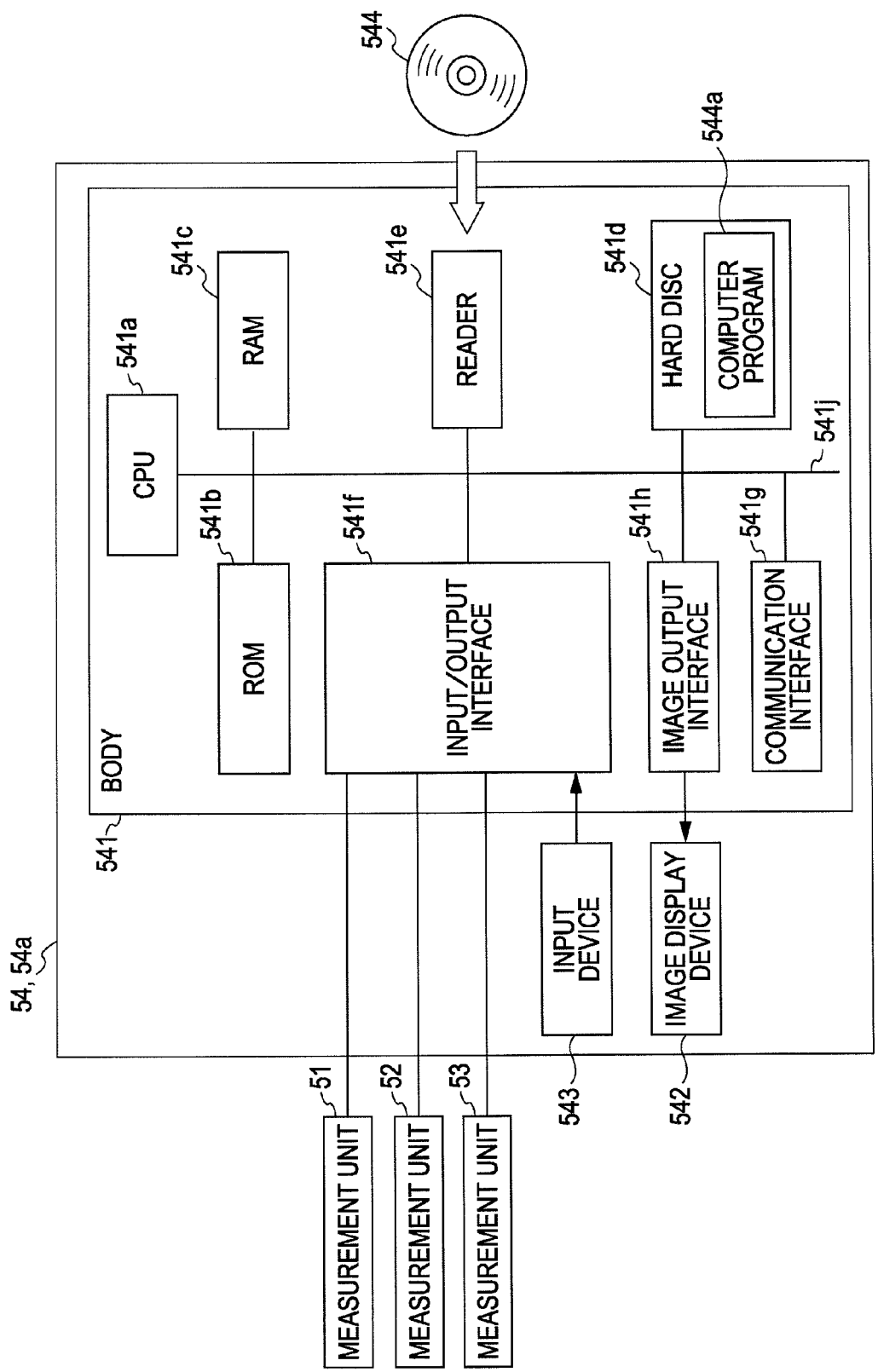
FIG. 3 is a block diagram illustrating a structure of an information processing unit provided in the blood cell analysis apparatus according to the embodiment.

FIG. 3 is a block diagram illustrating a structure of the information processing unit 54 according to the exemplary embodiment. A computer 54*a* makes the information processing unit 54 functional. As illustrated in FIG. 3, the computer 54*a* includes a body 541, an image display device 542, and an input device 543. The body 541 has a CPU 541*a*, a ROM 541*b*, a RAM 541*c*, a hard disc 541*d*, a reader 541*e*, an input/output interface 541*f*, a communication interface 541*g*, and an image output interface 541*h*. The CPU 541*a*, ROM 541*b*, RAM 541*c*, hard disc 541*d*, reader 541*e*, input/output interface 541*f*, communication interface 541*g*, and image output interface 541*h* are interconnected by a bus 541*j*.

The reader 541*e* is configured to read a computer program 544*a*, which is used to make the computer function as the information processing unit 54, from a transportable recording medium 544 and install the read computer program 544*a* in the hard disc 541*d*.

The input/output interface 541*f* is an interface, such as USB or IEEE1394, which is connected to the measurement units 51, 52, and 53 so as to communicate data with these measurement units.

The communication interface 541*g* is an Ethernet (registered trademark) interface, which is connected to the sample transport apparatus 3, system control apparatus 8, and test information management apparatus 9 so as to communicate with these apparatuses.

The information processing unit 54 controls the measurement unit 51, 52, 53 to carry out measurement of the sample and receives the measured data outputted from the measurement unit 51, 52, 53, and then analyzes the received measured data to generate a sample analysis result.

[Configuration of Smear Sample Production Apparatus 6]

The smear sample production apparatus 6 suctions the blood sample, puts a drop of the blood sample on a glass slide, and spreads the suctioned blood sample very thin on the glass slide. After the blood sample is dried, the smear sample production apparatus 6 drops a stain solution on the glass slide to stain the blood thereon so that a smear sample is obtained.

[Configuration of System Control Apparatus 8]

The system control apparatus 8 including a computer is in charge of controlling overall operations of the sample processing system 1. The system control apparatus 8 receives the rack ID and the sample ID from the sample dispatch apparatus 2 and checks with the test information management apparatus 9 about a measurement order of the received rack ID and sample ID. The system control apparatus 8 decides the transport destination of the sample rack and transmits a transport command indicating the transport destination to the sample transport apparatus 3.

A computer makes the system control apparatus 8 functional. The computer includes a body, an image display device, and an input device (not illustrated in the drawing). The body has a CPU, a ROM, a RAM, a hard disc, an input/output interface, and a communication interface. The computer constituting the system control apparatus 8 is configured similarly to the computer 54*a* constituting the information processing unit 54, therefore, detailed description of the computer is omitted.

[Configuration of Test Information Management Apparatus 9]

The test information management apparatus 9 is an apparatus provided in a facility for the management of any test-related information, generally called LIS (Laboratory Information System). The test information management apparatus 9 is connected not only to the blood cell analysis apparatus 5 but also to other clinical sample test apparatuses. The test information management apparatus 9 receives a measurement order inputted by the user or transmitted from an apparatus such as an electronic chart system, and stores and manages therein the received measurement order. Further, the test information management apparatus 9 receives a measurement order request inputted from the system control apparatus 8 or the blood cell analysis apparatus 5, and transmits the requested measurement order to the system control apparatus 8 or the blood cell analysis apparatus 5. The test information management apparatus 9 receives an analysis result from the blood cell analysis apparatus 5, and stores and manages therein the received analysis result.

The test information management apparatus 9 including a computer has, for example, a CPU, a ROM, a RAM, a hard disc, and a communication interface. The communication interface is connected to the LAN mentioned earlier and able to communicate with the system control apparatus 8 and the information processing unit 54 of the blood cell analysis apparatus 5. The hard disc stores therein the measurement orders. The measurement order contains therein information such as sample ID and target measurement items. The test information management apparatus 9, when requested by any other apparatus to transmit data of the measurement order including the sample ID, reads the measured data of the relevant sample ID from the hard disc and transmits the read data to the apparatus which requested the data. Any other functions of the test information management apparatus 9 are similar to the functions of the other computers described so far, therefore, are not described again.

[Operations of Sample Processing System]

Next, operations of the sample processing system according to the present exemplary embodiment are described.

First, a sample measurement operation of the blood cell analysis apparatus 5 according to the present exemplary embodiment is described. The operation described below is a sampler measurement operation in which the sample rack is automatically transported by the sample transport apparatus 3 and the samples held in the transported sample rack are automatically measured by the measurement units 51-53.

An initial step of the sample measurement operation using the sample processing system 1 is to start up the sample dispatch apparatus 2, sample transport apparatus 3, blood cell analysis apparatus 5, smear sample production apparatus 6, sample recovery apparatus 7, and system control apparatus 8.

Conventionally, the test information management apparatus 9 is an always-ON apparatus with no temporary halt. To start up the blood cell analysis apparatus 5, it is necessary to turn on all of the measurement units, 51, 52, and 53 and the information processing unit 54.

This section describes the startup of the information processing unit 54. When the information processing unit 54 is turned on, the CPU 541a of the information processing unit 54 executes initialization processes. The initialization processes include initialization of the RAM 541c and read of preset values. Then, the CPU 541a makes the image display device 542 display thereon a menu screen. Then, the startup of the information processing unit 54 is completed. After the menu screen is displayed, the information processing unit 54 can receive instructions inputted by the user. The menu screen will be described in detail later.

After the startup of the structural elements of the sample processing system 1 is completed, the sample measurement can start. Immediately after the startup, the measurement mode set in the measurement units 51, 52, and 53 of the blood cell analysis apparatus 5 is the sampler measurement mode.

When the user places the sample rack holding the sample containers in a rack housing unit 21 and inputs an instruction to start the sample processing to the sample processing system 1, the transport of the sample rack starts. The transport destination of the sample rack is decided by the system control apparatus 8, and the sample rack is transported by the sample transport apparatus 3 to the measurement unit decided as the transport destination.

The operation of the blood cell analysis apparatus 5 when the sample rack is transported to, for example, the measurement unit 51 is described. After the sample rack is transported to the measurement line 3M of the sample transport unit 3a, the sample container is transported to a suctioning position by the CPU 541a of the information processing unit 54, and the sample is suctioned from the sample container in a quantity necessary for the requested measurement item.

The CPU 541a of the information processing unit 54 controls the testing material preparing section 512 to prepare a testing material for measurement depending on the requested measurement item and supply the testing material to the detection section 513 so that the sample is measured by the detection section 513. After the sample measurement is over, the CPU 541a obtains the measured data outputted from the detection section 513. The CPU 541a analyzes the measured data and classifies the blood cells included in the sample into different categories. The CPU 541a further counts the blood cells in each of the categories to create a scattergram showing the categorized blood cells differently colored. A measurement result data obtained as a result of analyzing the measured data is stored in the hard disc with patient information included in the measurement order, and also transmitted to the system control apparatus 8 and the test information management apparatus 9. The blood cell analysis apparatus 5 performs the sample measurement operation described so far to all of the samples held in the sample rack sequentially.

A description of the other measurement units is omitted because the sample measurement operation is similarly carried out when the transport destination is the measurement unit 52 or 53.

The sample rack holding any sample, for which the production of a smear sample by the smear sample production apparatus 6 is requested, is transported to the measurement line 3M of the sample transport unit 4 so that the smear sample is produced.

After all of the samples held in the sample rack are measured as requested in the measurement order (or smear sample production), the sample rack is transported by the sample transport apparatus 3 to be recovered by the sample recovery apparatus 7.

<Screen Display Switch Operation>

Figure 4:
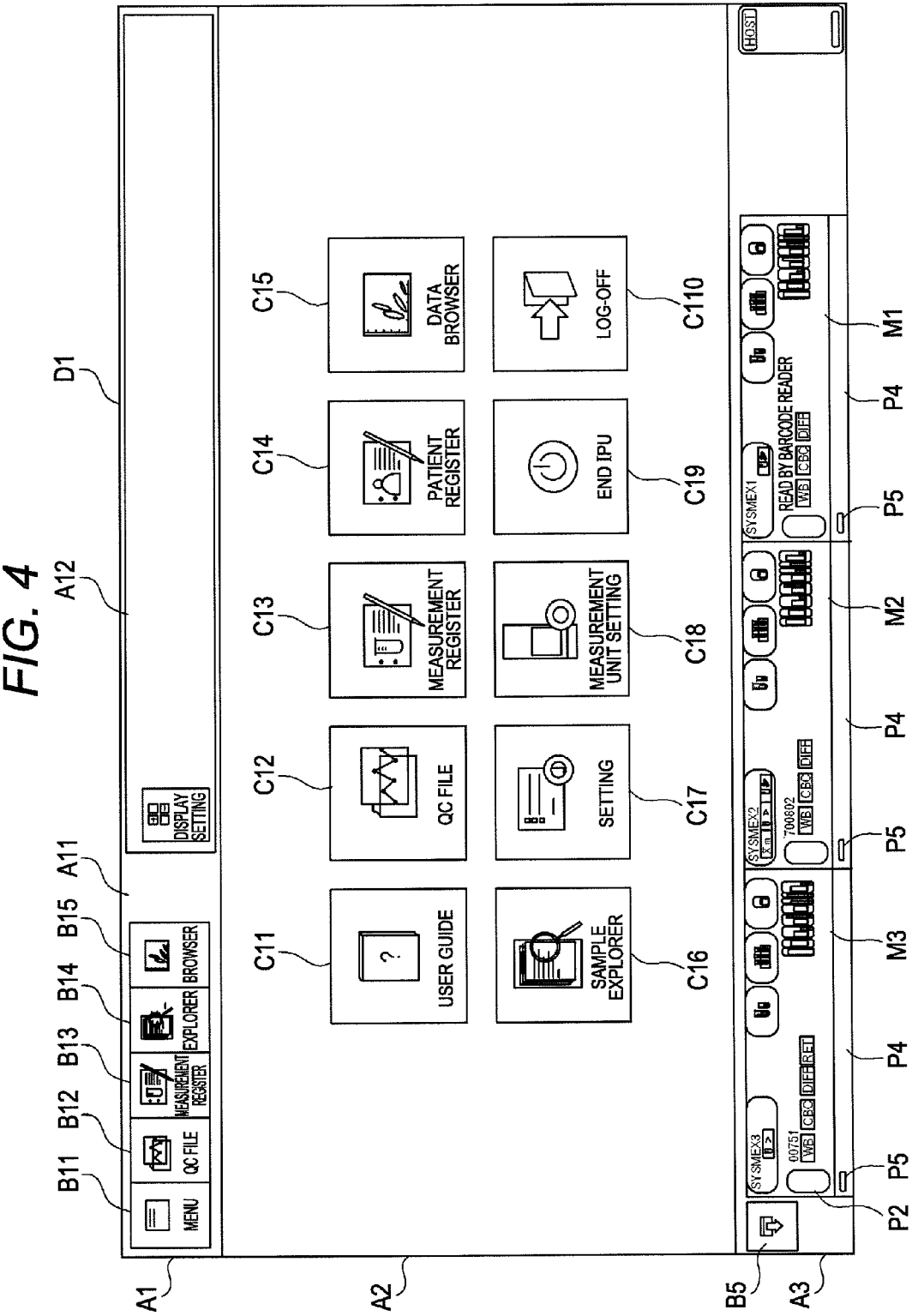
FIG. 4 is a drawing of a menu screen of the information processing unit.

FIG. 4 is a drawing of the menu screen of the information processing unit 54. A menu screen D1 is a screen displayed first after the startup of the information processing unit 54 is completed. The user can move on from the menu screen D1 to other screens, for example, a measurement result list screen, a measurement result detail screen, or an accuracy management screen.

As illustrated in the drawing, the menu screen D1 is provided with a tool bar region A1 where tool bars are displayed, a main region A2 where a plurality of icons used to open other screens are displayed, and a measurement operation region A3 used to manipulate the measurement units 51, 52, and 53. The tool bar region A1 and the measurement operation region A3 are not regions unique to the menu screen D1 but are common regions provided on other screens of the information processing unit. The tool bar region A1 is divided into a left-side region and a right-side region. The left-side region is a fixed button region A11 which displays the same buttons on any screens. The right-side region is a variable button region A12 where buttons displayed thereon are different on each screen. In the fixed button region A11 are displayed a "menu" button B11 used to display the menu screen, a "QC file" button B12 used to display the accuracy management screen, a "measurement register" button B13 used to display a measurement order register screen, an "explorer" button B14 used to display the measurement result list screen, and a "browser" button B15 used to display the measurement result detail screen. A "display setting" button used to set a display form of the menu screen D1 is displayed in the variable button region A12 on the menu screen D1.

The "icon" refers to an image assigned with a particular function and designed so as to symbolically represent the function. The "icon" includes those displayed in a window.

The tool bar region A1 is provided at the top of the screen. A main region A2 is provided below the tool bar region A1, and the measurement operation region A3 is provided further below. The main region A2 is a region having a larger area than the tool bar region A1 and the measurement operation region A3, where main content items of the screen are displayed. In the main region A2 of the menu screen D1 are displayed; a "user guide" icon C11 used to display a user guide, a "QC file" icon C12 used to display the accuracy management screen, a "measurement register" icon C13 used to display the measurement order register screen, a "patient register" icon C14 used to display a patient information register screen, a "data browser" icon C15 used to display the measurement result detail screen, a "sample explorer" icon C16 used to display the measurement result list screen, a "setting" icon C17 used to display an IPU setting screen where settings of the information processing unit 54 are inputted, a "measurement unit setting" icon C18 used to display a measurement unit setting screen where settings of the measurement units 51, 52, and 53 are inputted, an "IPU shutdown" icon C19 used to shutdown the information processing unit 54, and a "log-off" icon C110 used to log-off from the information processing unit 54. The icons C12-C18 are respectively assigned with functions of switching from the menu screen D1 to other screens. When any of the icons C12-C18 is clicked by way of a mouse, the menu screen D1 currently displayed is switched to a screen in response to the clicked icon. The button B12 is assigned with the same function as that of the icon C12. When the button B12 or the icon C12 is selected, a command to display the accuracy management screen is outputted by the CPU 541a, and the accuracy management screen is correspondingly displayed. Similarly, the button B13 is assigned with the same function as that of the icon C13, the button B14 is assigned with the same function as that of the icon C16, and the button B15 is assigned with the same function as that of the icon C15.

Figure 5:
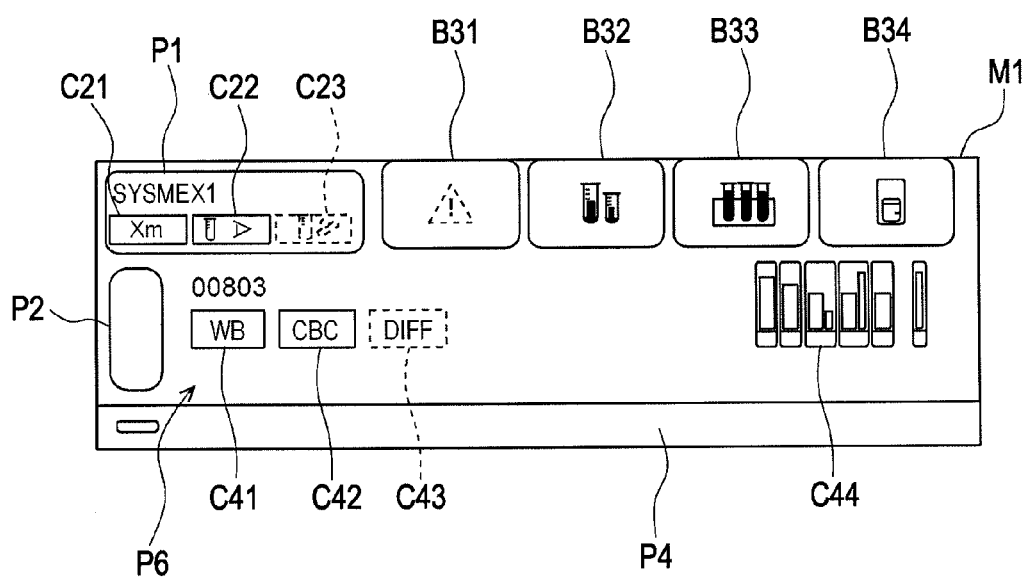
FIG. 5 is an enlarged view of a structure of a measurement unit operation section illustrated in FIG. 4.

Next, the measurement operation region A3 is described. The measurement operation region A3 is provided at the bottom of the screen D1 across the entire width of the screen D1. In the measurement operation region A3, measurement unit operation sections M1-M3 are displayed next to one another from left to right in an equal number to the measurement units (three according to the present exemplary embodiment). FIG. 5 is an enlarged view of a structure of the measurement unit operation section M1. The measurement unit operation section M1 is used to manipulate the measurement unit 51, the measurement unit operation section M2 is used to manipulate the measurement unit 52, and the measurement unit operation section M3 is used to manipulate the measurement unit 53. The measurement unit operation sections M1-M3 are positioned relative to one another in the same order as the measurement units 51-53. More specifically, the measurement unit operation section M1 used to manipulate the measurement unit 51 on the right (see FIG. 1) is similarly positioned on the right (see FIG. 4), the measurement unit operation section M2 used to manipulate the measurement unit 52 at the center (see FIG. 1) is similarly positioned at the center (see FIG. 4), and the measurement unit operation section M3 used to manipulate the measurement unit 53 on the left (see FIG. 1) is similarly positioned on the left (see FIG. 4).

On the upper left of the measurement unit operation section M1, a device status display section P1 is provided to display information as to the status of the measurement unit 51. The device status display section P1 displays a unit ID ("SYSTEM 1" in the illustration of FIG. 4) for identifying the measurement unit corresponding thereto (measurement unit 51 for the measurement unit operation section M1) and three icons C21, C22, and C23. The icon C21 indicates that an accuracy management (XbarM) function for ordinary samples is available. When the icon C21 is displayed, the XbarM function is available in the measurement unit. In the case where the XbarM function is not available in the measurement unit, the icon C21 is not displayed. The icon C22 indicates that a blood suctioning sensor of the measurement unit is set to ON. In the case where the blood suctioning sensor of the measurement unit is set to OFF, the icon C22 is not displayed. The icon C23 indicates that an "open measurement mode" is set, in which the sample is suctioned to be measured from an uncapped sample container having an upper end open. While the set measurement mode is a "closed measurement mode" in which the sample is suctioned to be measured from a capped sample container, the icon C23 is not displayed. The icon C23 illustrated in FIG. 5 with a broken line indicates that the icon C23 is not displayed.

To the right of the device status display section P1, four buttons, B31, B32, B33, and B34 are displayed. The button B31 is used when any error is generated in the measurement unit 51. When any error is generated in the measurement unit 51, a shape illustrated in the drawing with a broken line is displayed on the button B31 (hereinafter, called "error warning icon"). The error warning icon illustrated in FIG. 5 with a broken line indicates that the error warning icon is not displayed in the given example. When the button 31 is selected while the error warning icon is being displayed, a screen (window) reciting a handling method for the generated error is displayed with an overlap on a part of the main region A2 in an upper part of the measurement unit operation section M1. The user can resolve the error generated in the measurement unit 51 by checking the screen reciting the error handling method (hereinafter, called "error handling screen"). The error handling screen will be described in detail later.

The button B32 is used to display a measurement mode switch screen on which the measurement mode of the measurement unit 51 can be switched. When the button B32 is selected, the measurement mode switch screen is displayed with an overlap on a part of the main region A2 in the upper part of the measurement unit operation section M1. As a result of an input operation by the user to the measurement mode switch screen, one of the following measurement modes can be selected and set in the measurement unit 51; normal measurement mode, diluted measurement mode, humor measurement mode. The measurement mode switch screen will be described later in detail.

When the sampler measurement mode is set in the measurement unit 51, a shape corresponding to the sampler measurement mode (see FIG. 5) is displayed on the button B33. When the manual measurement mode is set in the measurement unit 51, a shape corresponding to the manual measurement mode is displayed on the button B33. When, for example, the button B33 is selected while the sampler measurement mode is currently set in the measurement unit 51, a sampler measurement screen used to request the sampler measurement operation is displayed with an overlap on a part of the main region A2 in the upper part of the measurement unit operation section M1. When, for example, the button B33 is selected while the manual measurement mode is currently set in the measurement unit 51, a manual measurement screen is displayed with an overlap on a part of the main region A2 in the upper part of the measurement unit operation section M1. Through an input operation to the sampler measurement screen, the user can request the sampler measurement operation for the measurement unit 51. When the user inputs an instruction to the manual measurement screen, the manual measurement operation can be requested for the measurement unit 51. The manual measurement screen will be described in detail later.

The button B34 is used to display a measurement unit menu screen on which operation instructions for the measurement unit 51 can be inputted. When the button B34 is selected, the measurement unit menu screen is displayed with an overlap on a part of the main region A2 in the upper part of the measurement unit operation section M1. As a result of an input operation by the user to the measurement unit menu screen, the accuracy management measurement, XbarM setting, and reagent replacement can be requested for the measurement unit 51. The measurement unit menu screen will be described in detail later.

Below the icon C21 of the device status display section P1, a status notifying section P2 is provided to notify the status of the measurement unit 51. The status notifying section P2 is a rectangular region displayed in green whenever the measurement unit 51 (measurement unit 52 for the measurement unit operation section M2, measurement unit 53 for the measurement unit operation section M3) is normally operating. The status notifying section P2 is displayed in red whenever the measurement unit 51 (measurement unit 52 for the measurement unit operation section M2, measurement unit 53 for the measurement unit operation section M3) is undergoing any abnormal status.

Below the device status display section P1 and to the right of the status notifying section P2, a sample number of the sample currently measured by the measurement unit 51 is displayed, and measurement items to be measured in the sample are displayed below the sample number. The icon C41 with "WB" indicates the "normal sample measurement mode". While the icon C41 is being displayed, the measurement unit 51 is in action in the normal sample measurement mode. When an icon with "PD" is displayed at the position of the icon C41, the measurement unit 51 is in action in the "diluted sample measurement mode". When an icon with "BF" is displayed at the position of the icon C41, the measurement unit 51 is in action in the "humor measurement mode". The normal sample measurement is to measure an undiluted blood sample (whole blood). The diluted sample measurement is to dilute the blood sample by a predetermined rate with a diluent (higher rate than in the normal sample measurement) before measuring the sample. The humor measurement is to measure humor in place of blood (for example, cerebrospinal fluid). When the measurement unit 51 is currently not performing the sample measurement, a sample number of the sample to be measured next is displayed with ">" appended to the top of it at a position to the right of the status notifying section P2.

To the right of the icon C41, icons C42 and C43 respectively corresponding to the discrete items "CBC" and "DIFF" are displayed. These icons C42 and C43 are provided for the discrete items that can be measured by the measurement unit 51. Because the measurement unit 51 is incapable of measuring "RET", there is no icon for "RET" in the measurement unit operation section M1. The measurement unit operation section M3 of the measurement unit 53 capable of measuring "RET" displays thereon an icon for "RET".

The icons C42 and C43 are displayed differently for one discrete item to be measured and another discrete item not to be measured in the measurement order of the sample currently displayed. An icon of the discrete item requested to be measured is displayed with a predetermined luminance (hereinafter, called "normal display"), whereas an icon of the discrete item not requested to be measured is displayed with a lower luminance than the normal display (hereinafter, called "shaded display"). When thus displayed, the item to be measured and the item not to be measured can be easily distinguished from each other. In FIG. 5, the icon C42 illustrated with a solid line is displayed in the normal display, whereas the icon C43 illustrated with a broken line is displayed in the shaded display. It is known from the illustration of FIG. 5 that the discrete item "CBC" is requested to be measured but the item "DIFF" is not requested to be measured in the sample numbered "00803".

To the right of the icons C42 and C43, a reagent residual quantity display icon C44 is displayed. The reagent residual quantity display icon C44 is used to display a reagent residual quantity in each of the reagent containers connected to the testing material preparing section 512 of the measurement unit 51. The reagent residual quantity display icon C44 has a plurality of frame-like shapes illustrating reagent containers connected to the testing material preparing section 514. The frame-like shapes of the respective reagent containers display therein indicators showing residual quantities of the reagents contained therein. The reagent containers connected to the testing material preparing section 512 have labels attached thereto in different colors respectively unique to different reagents (for example, red label attached to the coloring reagent for DIFF measurement, blue label attached to the diluent, etc.). The frame-like shapes included in the reagent residual quantity display icon C44 are displayed in the same colors as the labels of the reagent containers thereby represented, so that it is instantly known which frame-like shape and reagent container are paired with each other.

In an error message region P6 extending in a band shape at the bottom of the measurement unit operation sections M1 below the icons C41-C44, error messages are displayed when errors occur in the measurement unit 51. In the event that a particular reagent has run out, for example, an error message suggesting replacement of the reagent is displayed in this region (see FIG. 14).

The measurement unit operation sections M2 and M3, which are configured similarly to the measurement unit M1, are not described in this specification.

Below the measurement unit operation sections M1-M3 are provided transport error display sections P4, which are regions extending in a band shape where error messages are displayed when errors occur in the sample transport apparatus 3. The transport error display sections P4 display thereon error messages when errors occur in the sample transport apparatus 3 (see FIG. 14). The transport error display sections P4 are respectively provided for the sample transport units 3a-3c. The transport error display section P4 below the measurement unit operation section M1 is paired with the sample transport unit 3a provided in front of the measurement unit 51 for the measurement unit operation section M1. In the event of any error in the sample transport unit 3a, an error message notifying the error is displayed on the transport error display section P4. Similarly, the transport error display section P4 below the measurement unit operation section M2 is paired with the sample transport unit 3b provided in front of the measurement unit 52 for the measurement unit operation section M2, and the transport error display section P4 below the measurement unit operation section M3 is paired with the sample transport unit 3c provided in front of the measurement unit 53 for the measurement unit operation section M3. In the event of such a transport error that the sample rack is stuck on the transport path of the sample transport unit 3a, an error message notifying the transport error of the sample rack is displayed on the transport error display section P4 below the measurement unit operation section M1.

As illustrated in FIG. 4, a status notifying section P5 is provided on the left side of each transport error display section P4. The respective status notifying sections P5 are configured to notify the statuses of the sample transport units 3a-3c. The status notifying section P5 adjacent to the left side of the transport error display section P4 of the sample transport unit 3a is provided for the sample transport unit 3a. The status notifying section P5 located next to the left side of the transport error display section P4 of the sample transport unit 3b is provided for the sample transport unit 3b. The status notifying section P5 located next to the left side of the transport error display section P4 of the sample transport unit 3c is provided for the sample transport unit 3c. These status notifying sections P5 are elliptical regions that are laterally long and displayed in green while the sample transport units 3a-3c are normally operating. In the event of an abnormality in any of the sample transport units 3a-3c, the status notifying section P5 provided for the sample transport unit undergoing the abnormality is displayed in red.

When any of the buttons B31-B34 of the measurement unit operation sections M1-M3 is pressed, a screen responding to the pressed one of the buttons B31-B34 is displayed in an upper part of the measurement unit operation section M, M2, M3 so that the content currently displayed in the main region A2 is thereby hidden. However, these screens may be displayed at the same time, which will be described in detail later. For example, when the button B31 of the measurement unit operation section M1 is pressed and the button B32 of the measurement unit operation section M2 is then pressed while the screen reciting the error handling method is being displayed in the upper part of the measurement unit operation section M1, the measurement mode switch screen for the measurement unit 52 is displayed in the upper part of the measurement unit operation section M2. As illustrated in FIG. 4, a button B5 is provided to the left of the measurement unit operation section M3. The button B5 is used to have a plurality of displayed screens hidden at the same time or have the hidden screens displayed again. When the button B5 is pressed while the plurality of screens are thus displayed in an overlapping manner in the main region A2, all of the screens displayed at the time are hidden at once. When the button B5 is pressed while the plurality of screens are hidden, all of the screens hidden at the time are displayed again at once.

The main region A2 is a region shared by all of the measurement units 51-53. As illustrated in FIG. 4, the main region A2 of the menu screen D1 displays thereon icons that can be used for all of the measurement units 51-53. The accuracy management screen displays thereon accuracy management results obtained by the measurement units 51-53, and an icon C12 used to display the accuracy management screen can be used for any of the measurement units 51-53. The measurement result list screen displays thereon sample measurement results obtained by the measurement units 51-53, and an icon C16 used to display the measurement result list screen can be used for any of the measurement units 51-53. The measurement result detail screen displays thereon sample measurement results obtained by the measurement units 51-53 so that the sample measurement result of one sample is displayed in detail at a time, and an icon C15 used to display the measurement result detail screen can be used for any of the measurement units 51-53.

The measurement unit operation sections M1-M3 are each solely used for one of the measurement units 51-53. The measurement units operation sections M1-M3 are respectively unique to the measurement units 51-53 and each solely used to manipulate one of the measurement units.

Figure 6:
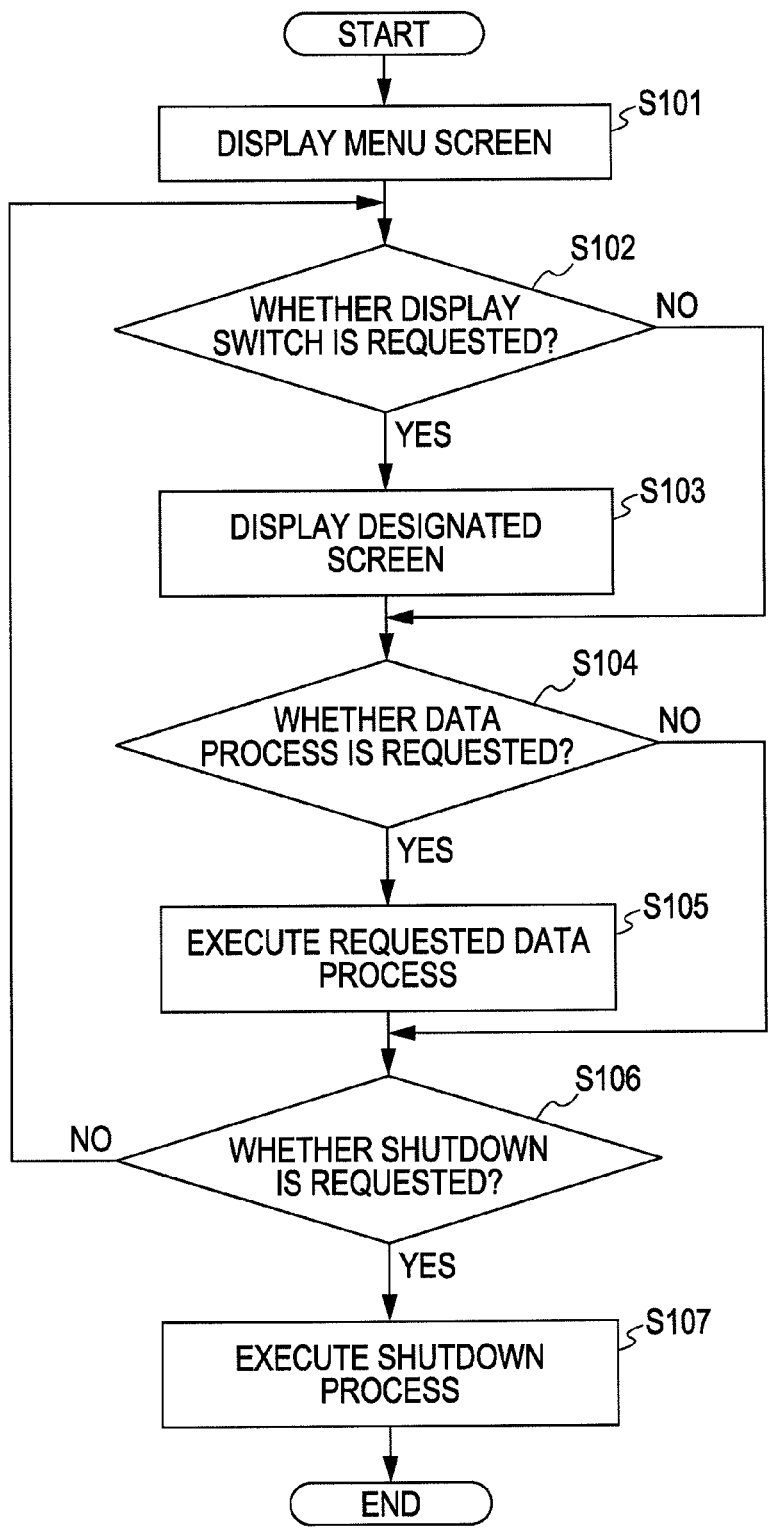
FIG. 6 is a flow chart illustrating processing steps for changing a screen display by the information processing unit.

FIG. 6 is a flow chart illustrating processing steps for switching the screen display operation by the information processing unit 54. As described earlier, when the information processing unit 54 starts to operate, the menu screen is displayed on the image display device 542 by the CPU 541a (Step S101). Then, the CPU 541a determines whether an instruction to switch the screen to be displayed is received (Step S102). As described earlier, when any of the icons C12-C18 displayed in the main region A2 of the menu screen D1 or any of the buttons B11-B15 displayed in the tool bar region A1 is selected, the user can request the information processing unit 54 to switch the screen to be displayed. The CPU 541a thus requested to switch the screen to be displayed (YES in Step S102) makes the image display device 542 display thereon any requested screen (Step S103). In the case where the CPU 541a did not receive the screen switch instruction (NO in Step S103), the operation proceeds to Step S104.

When any requested screen is displayed, the user can process data depending on the screen. When the measurement result list screen or the measurement result detail screen is displayed, for example, the measurement result can be displayed, and the selected (displayed) measurement result can be further validated upon an instruction inputted by the user. On the accuracy management screen, accuracy management data, which is a history of measurement results of materials accurately controlled, is displayed, and the accuracy management data may be outputted to and printed by an external printer, or transmitted to an external computer upon an instruction inputted by the user. The measurement order register screen is used to register the measurement orders. To register the measurement order, the user inputs an instruction to request the discrete item to be measured to the input device 53 and presses an execute button for register, so that the measurement order including the requested discrete item is stored in a measurement order database, not illustrated in the drawing, provided in the hard disc 541d. The patient information register screen is used to register the information of patients. To register the patient information, the user inputs the patient information, for example, patient IDs, patient names, and attending doctors and presses an execute button for register, so that the inputted patient information is stored in a patient information database provided in the hard disc 541d. As described so far, the CPU 541a determines whether the data process instruction depending on the displayed screen is received (Step S104). In the case where the CPU 541a determines that the data process instruction was not received (NO in Step S104), the operation proceeds to Step S106.

When the CPU 541a determines in Step S104 that the data process instruction was received (YES in Step S104), the requested data process is executed (Step S105), and the operation proceeds to Step S106.

In Step 106, the CPU 541a determines whether an instruction to shutdown the information processing unit 54 is received (Step S106). While the menu screen D1, for example, is being displayed, it can be requested to shutdown the information processing unit 54 by selecting the icon C19. In the case where the CPU 541a determines in Step 106 that the instruction to shutdown the information processing unit 54 was not received (NO in Step S106), the operation returns to Step S102 to determine again whether the screen switch instruction is received (Step S102). While any screen but the menu screen D1, for example, is being displayed, the process of Step S102 is to determine whether any of the buttons B11-B15 displayed on the tool bar region A1 is selected.

When the CPU 541a determines in Step S106 that the instruction to shutdown the information processing unit 54 was received (YES in Step S106), the CPU 541a executes a shutdown process (Step S107), and ends the operation.

Figure 7:
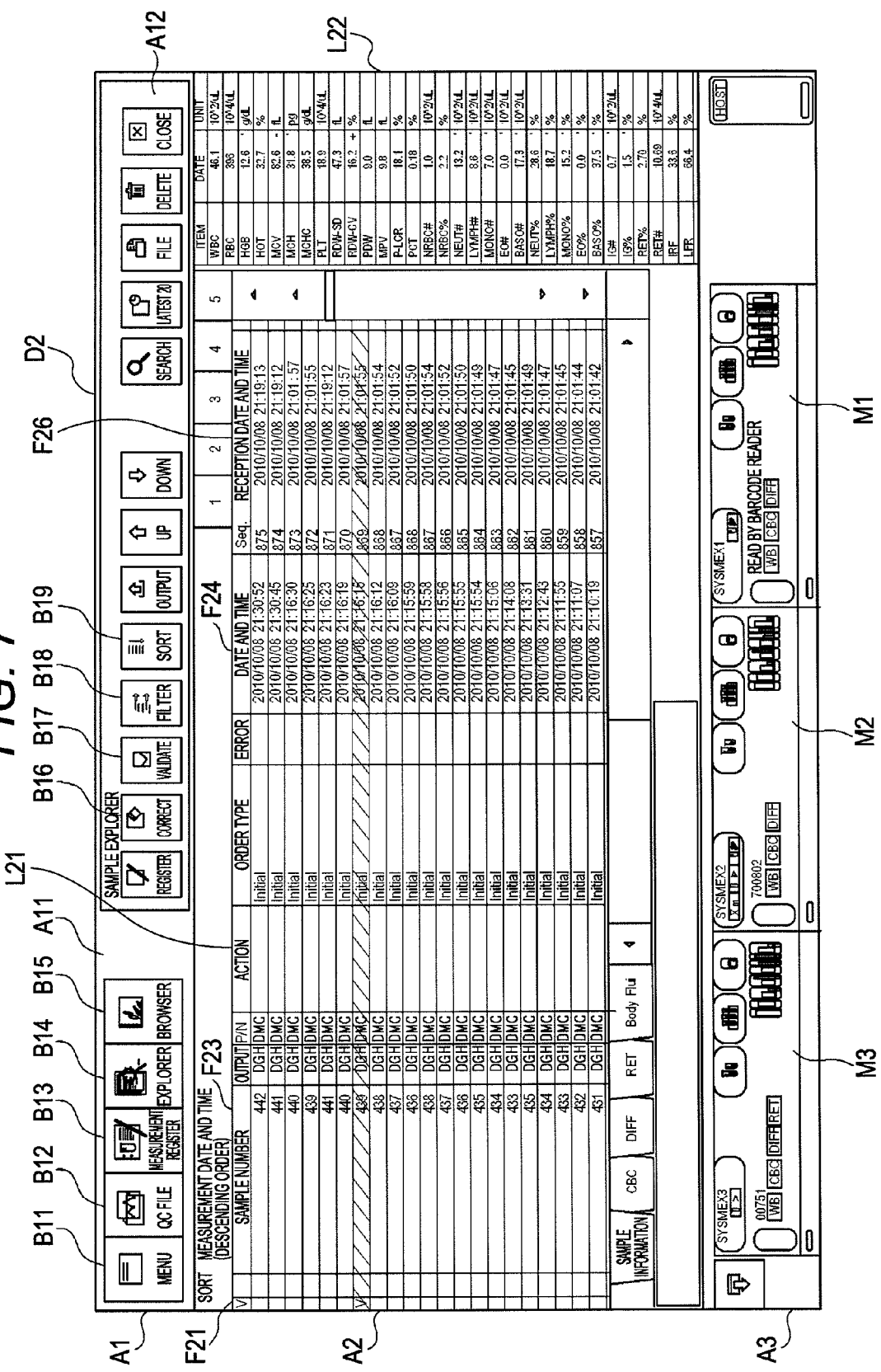
FIG. 7 is a drawing of a measurement result list screen of the information processing unit.

Next, the operation of the information processing unit 54 when the screen currently displayed is switched to the measurement result list screen is described. FIG. 7 is a drawing of the measurement result list screen of the information processing unit 54.

Similarly to the other screens, a measurement result list screen D2 is provided with a tool bar region A1, a main region A2, and a measurement operation region A3. A fixed button region A11 of the tool bar region A1 and the measurement operation region A3 display thereon items similar to those of the menu screen D1, therefore, description of the displayed items in these regions is omitted.

The main region A2 of the measurement result list screen D2 displays a sample information list. As illustrated in FIG. 7, a sample information list L21 shows information of each sample in each row. The sample information list L21 is provided with a field F21 where whether the measurement results are validated, which will be described later, is shown, a field F23 where sample numbers are shown, a field F24 where measurement dates and times are shown, and a field F26 where dates and times when the measurement orders were received are shown. The main region A2 thus collectively displaying thereon the information of samples measured by the measurement units 51-53 is shared by the measurement units 51-53 to display the information obtained by these measurement units.

Any of the rows in the sample information list L21 can be selected by click of a mouse. To the right of the sample information list L21 is displayed a measurement result list L22 which displays the sample measurement results. When one sample information is selected, the measurement result list L22 displays thereon a list of numeral data in the measurement result of the selected sample.

On the measurement result list screen D2, the sample measurement result can be validated, and other data processes can be performed to the measurement result. A variable button region A12 of the measurement result list screen D2 is provided with, for example, a "correct" button B16 used to correct the sample information, a "validate" button B17 used to validate the sample measurement result, a "filter" button B18 used to display only the sample information which meets a particular requirement on the sample information list L21, and a "sort" button B19 used to sort the sample information in different orders on the sample information list L21.

To validate the measurement result, the user selects one sample information displayed on the sample information list L21 as illustrated in the drawing. A row indicated with diagonal lines in FIG. 7 indicates the selected sample information. The user confirms the measured data in each item displayed on the measurement result list L22. When the user decides that the measurement result should be reported to a doctor, he selects the "validate" button B17 so that the selected measurement result is validated. In the field F21 of the validated sample information, "V" is displayed, indicating "already validated", and information indicating that the measurement result was validated is registered in a measurement result database provided in the hard disc 51d.

Figure 8:
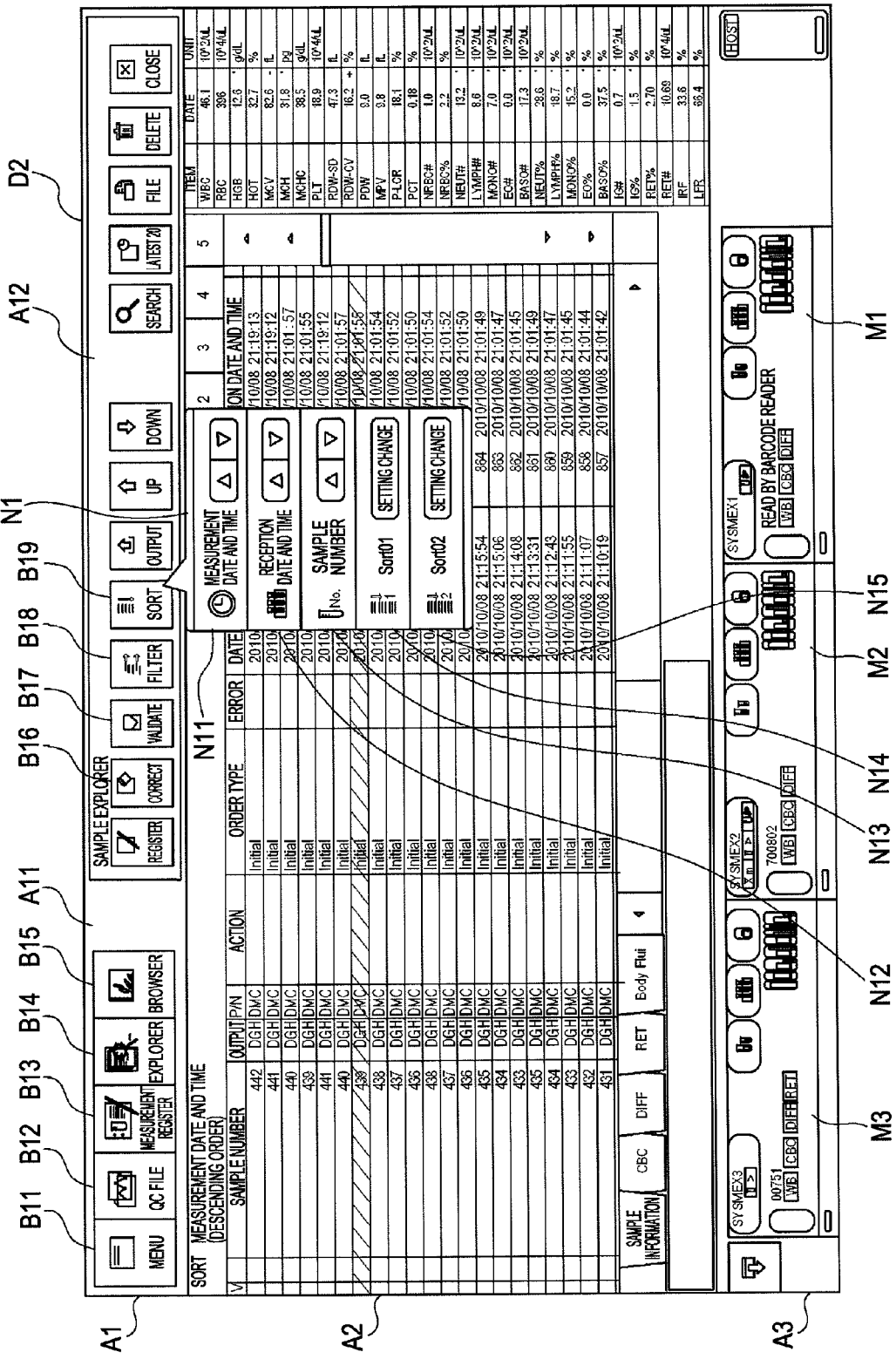
FIG. 8 is a drawing of the measurement result list screen with a menu displayed thereon.

This section describes how the sample information can be sorted in different orders. The button B19 is used to sort the sample information displayed on the sample information list L21 in different orders. When the button B19 is selected, a sorting order setting menu is displayed below the button B19. FIG. 8 is a drawing of the measurement result list screen with the menu displayed thereon. As illustrated in FIG. 8, when the button B19 is selected, a menu N1 is displayed below the button B19, overlapping on the sample information in the main region A2. The menu N1 is provided with a menu item N11 for sorting the sample information based on measurement dates and times, a menu item N12 for sorting the sample information based on dates when the measurement orders were received, and a menu item N13 sorting the sample information based on sample numbers. Any of the menu items N11-N13 can be selected by the user, and the sample information can be sorted in a different order based on the condition predefined in the selected menu item. The menu items N11-N13 have buttons respectively provided to choose one of ascending and descending orders. When one of the buttons is clicked by the user, one of the ascending and descending orders can be selectively set.

The menu N1 further has menu items N14 and N15 that can be set by the user. When a "setting change" button provided in the menu item N14, N15 is selected, a dialogue screen for setting a sorting condition is displayed (not illustrated in the drawing), so that the user can additionally set a new sorting condition.

To let the user readily know that the displayed menu N1 results from selecting the button B19, the menu N1 is displayed in a balloon with a triangular tip sticking out from its top of the menu N1 pointing to the bottom 19. When any of the other buttons is selected, a menu is similarly displayed in a balloon with its triangular tip pointing to the selected button. This helps the user to readily know which of the buttons is the origin of the menu currently displayed.

Figure 9:
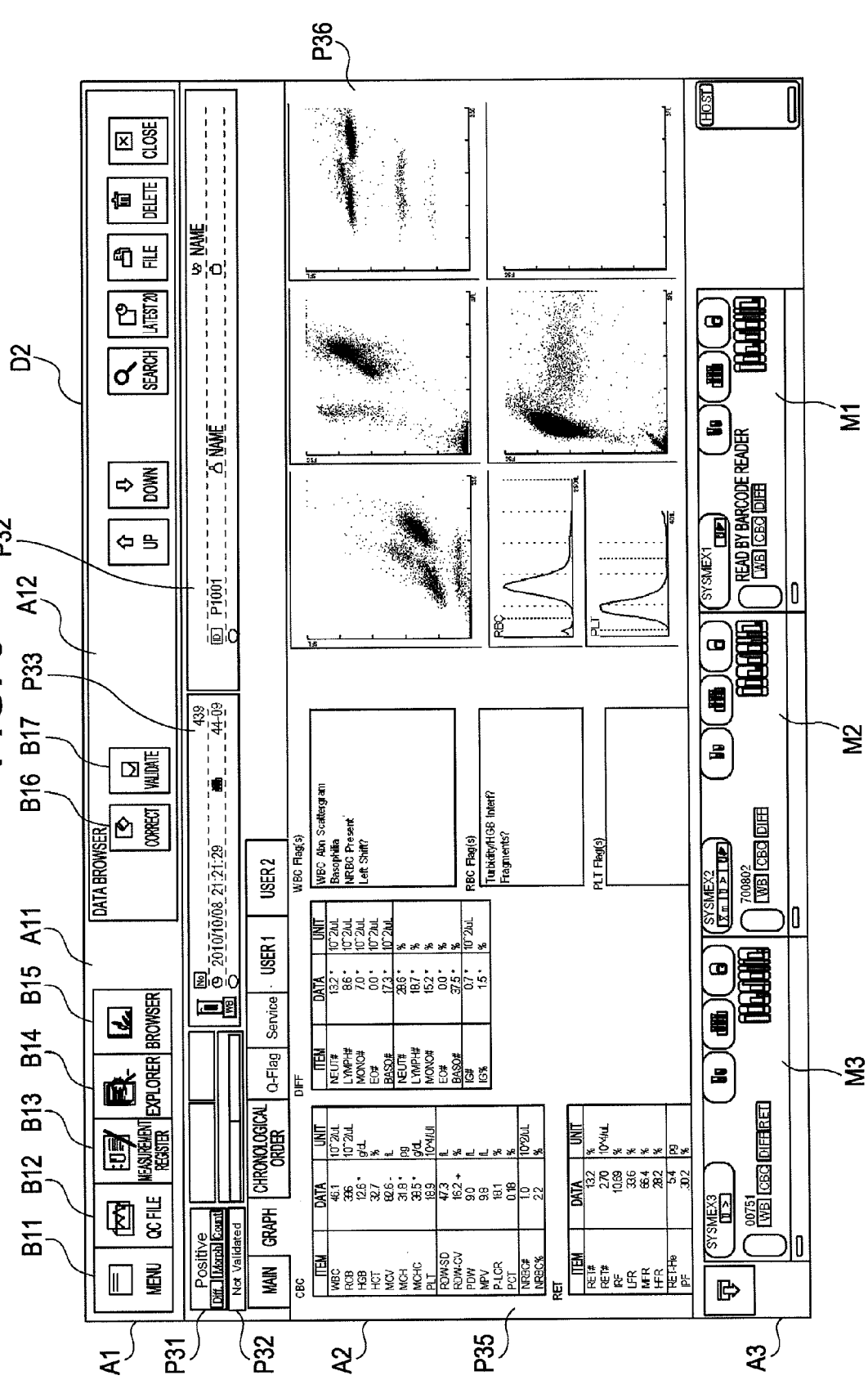
FIG. 9 is a drawing of a measurement result detail screen of the information processing unit.

Next, the measurement result detail screen is displayed. FIG. 9 is a drawing of the measurement result detail screen.

Similarly to the other screens, a measurement result detail screen D3 is provided with a tool bar region A1, a main region A2, and a measurement operation region A3. A fixed button region A11 of the tool bar region A1 and the measurement operation region A3 display thereon items similar to those of the menu screen D1, therefore, description of the displayed items in these regions is omitted.

The main region A2 of the measurement result detail screen D3 displays thereon numeral data and figurative data (distribution chart) of the sample measurement result obtained by any of the measurement units 51-53. Referring to FIG. 9, an upper part of the main region A2 displays thereon a region P31 showing positive result information indicating that the measurement result is positive when any of the measurement results currently displayed is positive, meaning that the measurement result includes some abnormality beyond a predefined normal range, a region P32 showing validation information indicating whether the measurement result currently displayed has been validated, a region P33 showing the sample information such as sample number and measurement date and time, and a region P34 showing the patient information such as patient name, patient ID, and attending doctor. The main region A2 illustrated in FIG. 9 only displays the measurement result of the sample measured by one of the measurement units 51-53. However, the measurement result currently displayed in the main region A2 can be switched to the measurement result of the sample measured by either of the other two measurement units. Thus, the main region A2 is shared to display all of the information obtained from the measurement units 51-53.

A region P35 which displays numeral data of the measurement result is provided below the regions P31-P34 on the left side of the main region A2, and a region P36 which displays distribution chart data of the measurement result is provided below the regions P31-P34 on the right side of the main region A2. The region P35 displays the numeral data of the respective measurement items in the form of a table. The region P36 displays scattergrams and histograms created based on the sample measurement.

The measurement result detail screen D3 thus characterized is used to validate and correct the sample measurement results. A variable button region A12 of the measurement result detail screen D3 is provided with, for example, a "correct" button B16 used to correct the sample information, and a "validate" button B17 used to validate the sample measurement result.

To validate the measurement result, the user confirms the measured data and distribution chart data of the respective items displayed in the regions P35 and P36 in the drawing, and the user selects the "validate" button B17 when he decides to report the measurement result to a doctor. The measurement result currently selected is thus validated. After the validation is completed, information indicating that the measurement result has been validated is displayed in the region P32. Then, the information indicating that the measurement result has been validated is registered in the measurement result database of the hard disc 51d.

<Display of Measurement Operation Menu>

While any of the screens described so far is being displayed, the measurement unit operation sections M1-M3 are constantly displayed. While any of the screens described so far is being displayed, the user can input the instructions to the measurement unit operation sections M1-M3 to thereby manipulate the measurement units 51-53. A screen display when the measurement unit operation sections M1-M3 are operated is hereinafter described.

Figure 10:
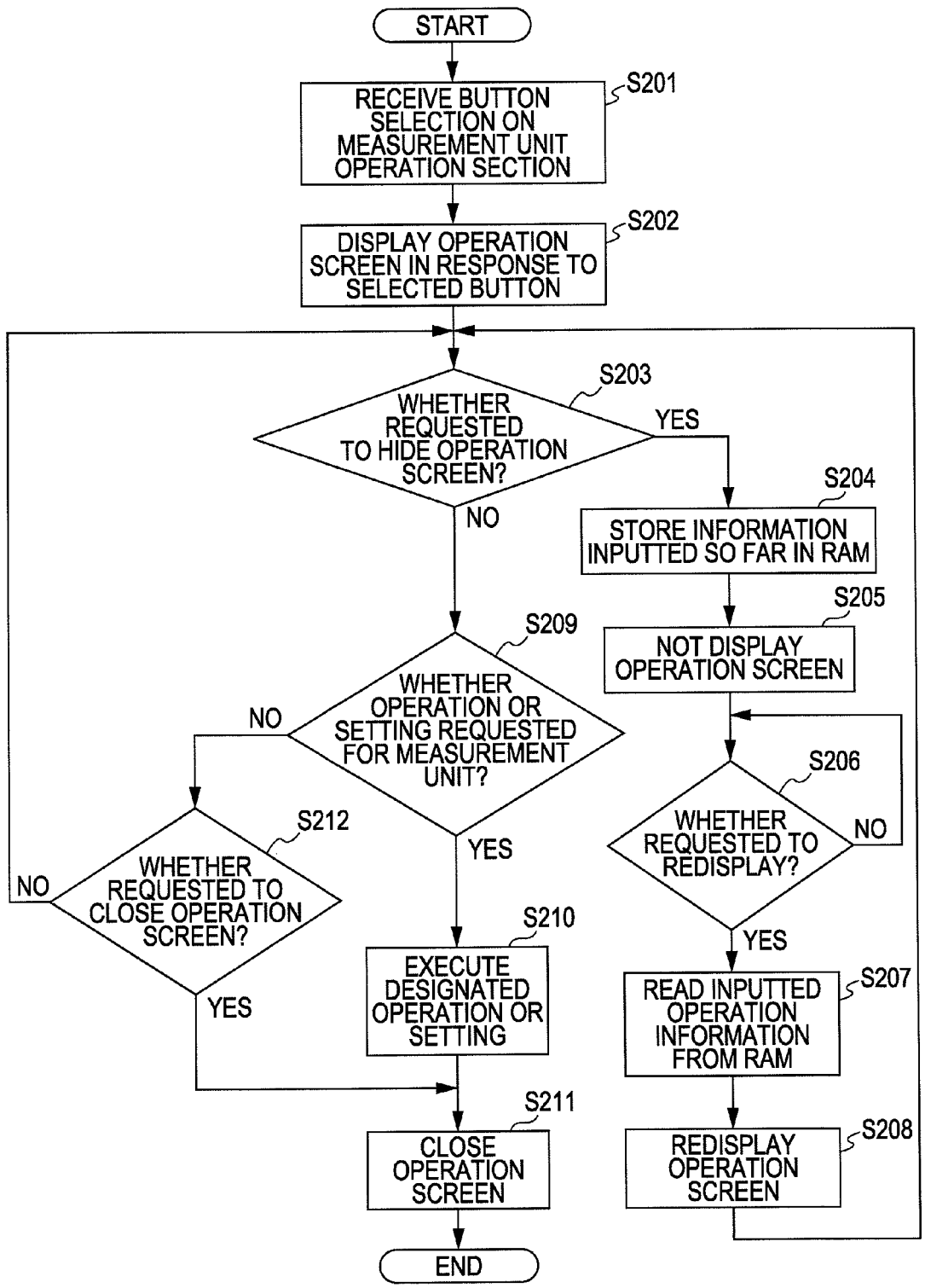
FIG. 10 is a flow chart illustrating processing steps for displaying a measurement operation menu by the information processing unit.

FIG. 10 is a flow chart illustrating processing steps for displaying a measurement operation menu by the information processing unit 54. The user inputs the instructions to the measurement unit operation sections M1-M3 by handling the input device 543 of the information processing unit 54 to make the measurement units 51-53 operate based on the instructions. Any of the buttons B31-B34 of the measurement unit operation section M1-M3 can be arbitrarily selected by the user. When one of the buttons B31-B34 is selected, a corresponding screen (including menu) is displayed. Through an input operation to these screens (hereinafter, "operation screens"), the user can variously set or manipulate the measurement unit 51.

The CPU 541*a* receives the user's selection of one of the buttons B31-B34 of the measurement unit operation sections M1-M3 (Step S201). When the CPU 541*a* receives the user's selection of one of the buttons B31-B34 of the measurement unit operation sections M1-M3, the process of Step S202 is called.

Figure 11:
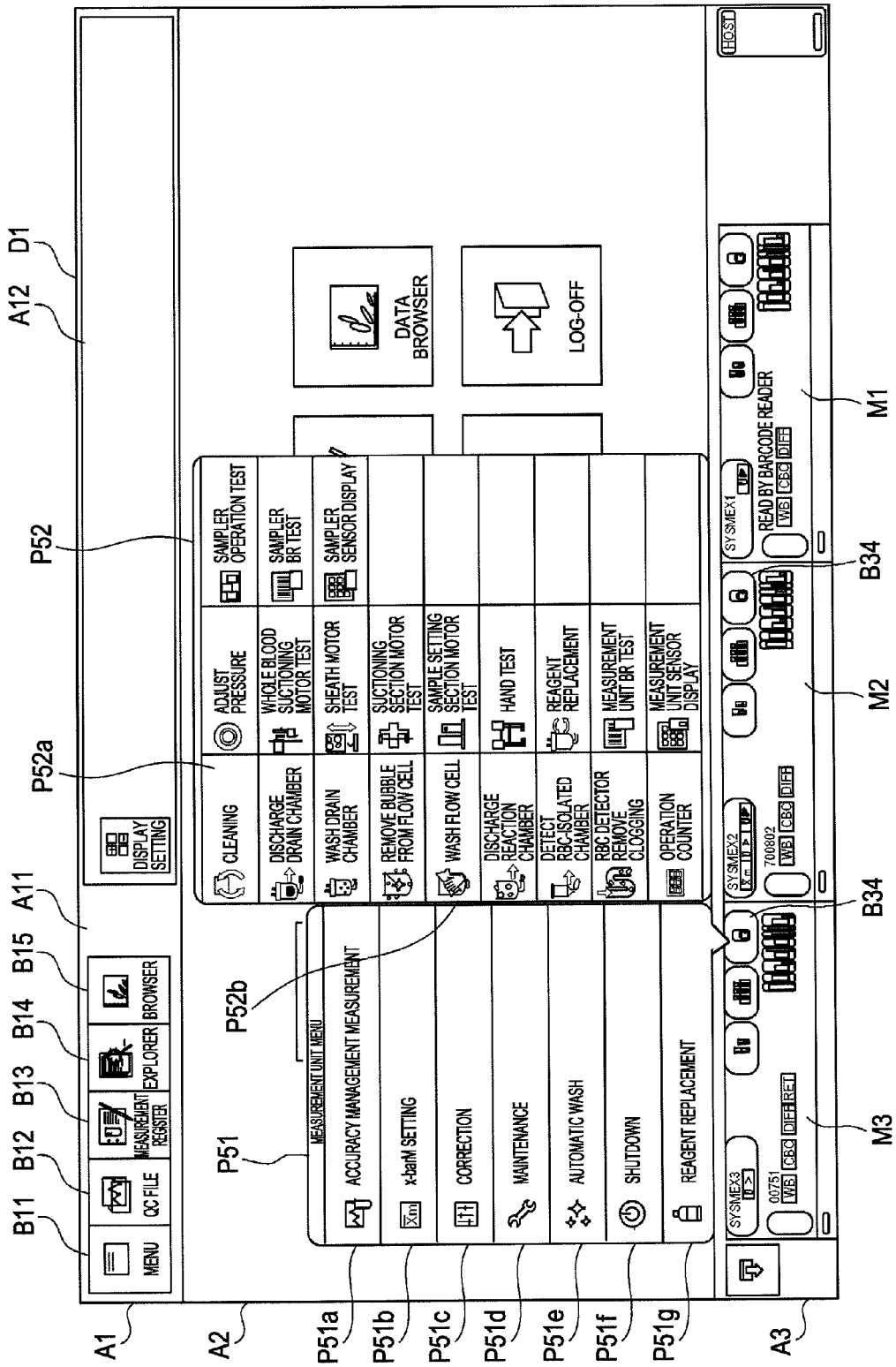
FIG. 11 is a drawing of an operation section menu screen.

In Step S202, the CPU 541*a* displays an operation screen demanded by the selected button as illustrated in FIG. 11 (Step S202). At a position in an upper part of the measurement unit operation section where the selected button is provided in the main region A2, the operation screen is displayed near the measurement unit operation section. To help the user to readily know that the operation screen is displayed in response to the selected button, as shown in FIG. 11, the operation screen is displayed in a balloon with its triangular tip pointing to the selected button.

While the operation screen called up by the selected one of the buttons B31-B34 is being displayed, the user may have to access the tool bar region A1 or the main region A2. According to the present exemplary embodiment, when one of the buttons B31-B34 is selected to display the operation screen demanded by the selected button and the user selects again the already selected button (button which called up the operation screen currently displayed), information so far inputted to the operation screen called up by the button is stored, and the operation screen is then hidden so that the user can perform the input operation to the tool bar region A1 or the main region A2. Accordingly, the present exemplary embodiment can temporarily suspend the display of the operation screen called up by the selected button to allow the tool bar region A1 or the main region A2 to be accessed without losing the information so far inputted.

Further, the present exemplary embodiment can hide the operation screen called up by the selected button when an arbitrary section of the tool bar region A1 or the main region A2 is selected while the operation screen is being displayed after any of the buttons B31-B34 is pressed. When the arbitrary section is thus accessed while a plurality of operation screens are being displayed, all of the operation screens displayed at the time are hidden, but all of the information inputted to any of the operation screens is safely stored.

A plurality of operation screens can be similarly hidden at the same time when the button B5 (see FIG. 4) provided on to the left of the measurement unit operation section M3 is pressed. For example, when any of the buttons B31-B34 is pressed in at least two of the measurement unit operation sections M1-M3 and the button B5 is then pressed while at least two operation screens are being displayed, all of the operation screens are hidden at once, but all of the information inputted to any of the operation screens is safely stored.

The CPU 541*a* determines whether an instruction to hide the operation screen is received (Step S203). When the CPU 541*a* determines that the instruction was received (YES in Step S203), the CPU 541*a* stores the information so far inputted to the operation screen in the RAM 541*c* (Step S204), and then hide the operation screen (Step S205). After that, the user can input the information to the tool bar A1 or the main region A2.

The CPU 541*a* determines whether an instruction to redisplay the hidden operation screen is received (Step S206). After the operation screen is hidden, a button indicating that the operation screen is hidden (not illustrated in the drawing) is displayed at a position of one of the buttons B31-B34 of the measurement unit operations sections corresponding to the hidden operation screen in place of the buttons B31-B34. When the button is selected, the operation screen so far hidden is redisplayed in a state immediately before it was hidden. When the button B5 is selected while the operation screen is being hidden, the operation screen so far hidden can be similarly redisplayed. The button B5 can redisplay a plurality of operation buttons at once. When the button B5 is pressed while a plurality of operation screen are being hidden, all of the hidden operation screens are redisplayed in a state immediately before they were hidden.

When the CPU 541*a* determines in Step S206 that the instruction to redisplay the hidden operation screen was not received (NO in Step S206), the operation returns to Step S206. Then, the tool bar region A1 or the main region A2 can be displayed and used until the redisplay instruction is inputted.

When the CPU 541*a* determines in Step S206 that the instruction to redisplay the hidden operation screen was received (YES in Step S206), the CPU 541*a* reads the inputted information stored in the RAM 541*c* (Step S207) and redisplays the operation screen so far hidden on the display device 542 (Step S208). Then, the CPU 541*a* returns the operation to Step S203.

When the CPU 541*a* determines in Step S203 that the instruction to hide the operation screen was not received (NO in Step S203), the CPU 541*a* determines whether the input to the operation screen, such as an instruction to operate or set the measurement units 51-53, is received (Step S209). When the CPU 541*a* determines in Step S209 that the input to the operation screen was received (YES in Step S209), the CPU 541*a* executes a process to operate or set the measurement unit operation (Step S210), and then closes the operation screen (Step S211) to end the operation. When the CPU 541*a* determines that the operation of the measurement unit was instructed in Step S210, the measurement unit is controlled to operate as instructed. When the CPU 541*a* determines that the setting of the measurement unit was instructed in Step S210, setting information of the measurement unit stored in the hard disc 541*d* is updated with newly inputted set values. When, for example, an instruction for manual sample measurement in the measurement unit 51 was received, the CPU 541*a* controls the measurement unit 51 to perform the manual sample measurement. When, for example, an instruction for reagent replacement in the measurement unit 52 was received, the CPU 541*a* controls the measurement unit 52 to replace the reagent.

When determined in S209 that the input to the operation screen was not received (NO in Step S209), the CPU 541*a* determines whether an instruction to close the operation screen is received (Step S212). The instruction to close the operation screen, which is different to the instruction to hide the operation screen, is to delete the information so far inputted to the operation screen and then make the operation screen hidden. When a cancel button displayed on the operation screen is pressed by the user, the instruction to close the operation screen can be inputted to the information processing unit 54. When the CPU 541*a* determines that the instruction to close the operation screen was received in Step S212 (YES in Step S212), the CPU 541*a* proceeds to Step S211 to close the operation screen (Step S211), and then ends the operation. When the CPU 541*a* determines that the instruction to close the operation screen was not received in Step S212 (NO in Step S212), the CPU 541a returns the operation to Step S203.

Next, a screen display when the measurement unit is instructed to perform maintenance is described in detail. When the button B34 of the measurement unit operation sections M1-M3 is selected, an operation menu screen is displayed. FIG. 11 is a drawing of the operation menu screen. An operation menu screen P51 is provided with a menu item P51a selected to make the measurement unit execute the accuracy management measurement, a menu item P51b selected to make the measurement unit execute the XbarM setting, a menu item P51c selected to make the measurement unit execute correction, a menu item P51d selected to make the measurement unit execute the maintenance, a menu item P51e selected to make the measurement unit execute an automatic wash, a menu item P51f selected to make the measurement unit shutdown, and a menu item P51g selected to make the measurement unit replace the reagent. Any of the menu items P51a-P51g can be selected by the user by way of the input device 543. When one of the menu items is selected, an operation instruction or a setting instruction corresponding to the selected menu item is issued by the CPU 541a.

As illustrated in FIG. 11, the operation menu screen P51 is displayed immediately above the measurement unit operation section M3 provided with the selected button B34 in vicinity of the measurement unit operation section M3. The operation menu screen P51 has a width dimension equal to that of the measurement unit operation section M3. When one of the buttons B31-B34 is selected, the operation screen as large as the measurement unit operation section in width is displayed immediately above the measurement unit operation section provided with the selected button. This prevents the operation screens of the adjacent measurement units from overlapping on each other when they are displayed at the same time.

When the menu item P51d of the operation menu screen P51 is selected, a maintenance menu screen P52 is displayed to the right of the operation menu screen P51. The maintenance menu screen P52 is provided with a plurality of menu items used to make the measurement unit execute the maintenance. The menu items of the maintenance menu screen P52 include, for example, a menu item P52a selected to clean the measurement unit 53, and a menu item P52b selected to wash the detection section 513 of the measurement unit 53.

A manual measurement is described below. Describing the manual operation, the sample contained in the sample container manually set by the user in any of the measurement units 51, 52, and 53 is measured by the measurement unit in which the sample container is set. Hereinafter, the manual measurement by the measurement unit 51 is described.

To execute the manual measurement, it is necessary that the manual measurement mode be set in the measurement unit 51. In the case where the manual measurement mode is not set in the measurement unit 51, the user presses a mode setting switch (not illustrated in the drawing) provided in a housing of the measurement unit 51, so that the measurement mode currently set in the measurement unit 51, which is the sampler measurement mode, is shifted to the manual measurement mode.

Figure 12:
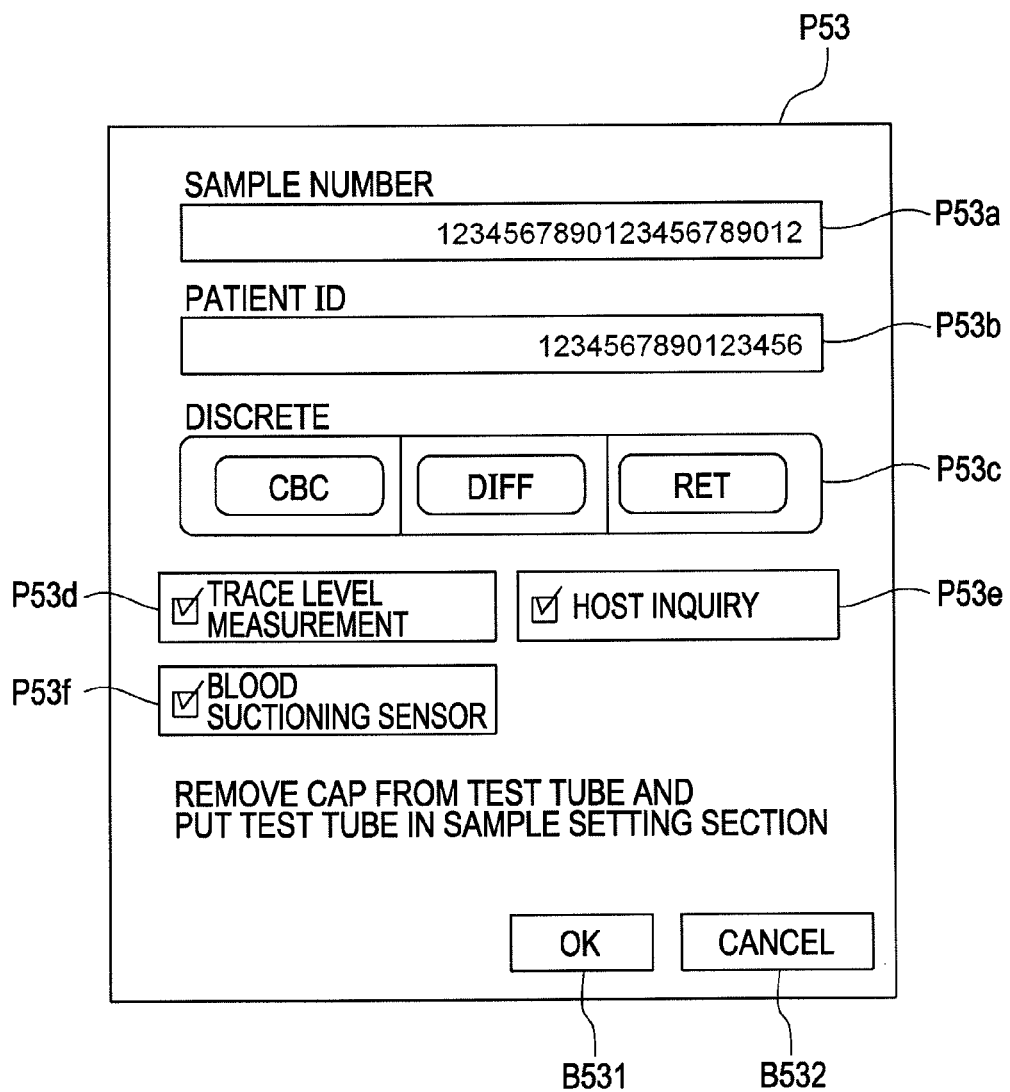
FIG. 12 is a drawing of a manual measurement screen.

When the manual measurement mode is set in the measurement unit 51, a shape indicating the manual measurement mode is displayed on the button B33 of the measurement unit operation section M1 used to operate the measurement unit 51. When the button B33 is pressed, a manual measurement screen having a width dimension equal to that of the measurement unit operation section M1 is displayed immediately above the measurement unit operation section M1. FIG. 12 is a drawing of the manual measurement screen. A manual measurement screen P53 is provided with an input region P53a used to input a sample number, an input region P53b used to input patient ID, a selection region P53c used to select the discrete item to be measured, a selection region P53d used to request a trace level measurement, a selection region P53e used to request an inquiry of the measurement order to the test information management apparatus 9, a selection region P53f used to turn on a blood suctioning sensor, a button B531 used to start the manual measurement, and a button B532 used to cancel the input to the manual measurement screen P53 and hide the manual measurement screen P53.

The user inputs information necessary for the manual measurement to the manual measurement screen P53 and then selects the button B531 to request the information processing unit 54 to perform the manual sample measurement in the measurement unit 51. The user then presses a switch (not illustrated in the drawing) provided in a housing of the measurement unit 51 to request the information processing unit 54 to move the sample container transport section 515 of the measurement unit 51 out of the housing. Then, the CPU 541a of the information processing unit 54 controls the measurement unit 51 to make the sample container transport section 515 be moved out of the housing of the measurement unit 51. The user places an uncapped sample container at a sample container holding position of the sample container transport section 515 when the set mode is an open measurement mode. On the other hand, the user places a capped sample container at the sample container holding position of the sample container transport section 515 when the set mode is a closed measurement mode. Then, the user presses the switch provided in the housing of the measurement unit 51 to request the information processing unit 54 to fetch the sample container into the measurement unit 51. The CPU 541a controls the measurement unit 51 to make the sample container transport section 515 be moved into the housing of the measurement unit 51.

The CPU 541a of the information processing unit 54 controls the sample container transport section 515 to transport the sample container to a suctioning position, while controlling the sample suctioning section 511 to suction the sample from the sample container in a quantity necessary for the measurement item requested in the selection region P53c of the manual measurement screen P53. After the sample suctioning is completed, the CPU 541a makes the sample container transport section 515 be moved out of the measurement unit 51 to remove the sample container from the measurement unit 51. The user removes the sample container from the sample container transport section 515. When the user continues to manually measure the other samples, he places the other sample containers again in the sample container transport section 515.

The CPU 541a of the information processing unit 54 controls the testing material preparing section 512 to prepare the testing material for measurement depending on the measurement item requested in the selection region P53c of the manual measurement screen P53, and supplies the testing material to the detection section 513 so that the detection section 513 performs the sample measurement. After the sample measurement is over, the CPU 541a obtains the measured data outputted from the detection section 513. The CPU 541a analyzes the measured data similarly to the sampler measurement operation to obtain the sample measurement result for the measurement item requested in the selection region P53c of the manual measurement screen P53. The measurement result data generated by analyzing the measured data is stored in the hard disc.

A description of the other measurement units is omitted because the same sample measurement operation is similarly carried out when the transport destination is the measurement unit 52 or 53.

Figure 13:
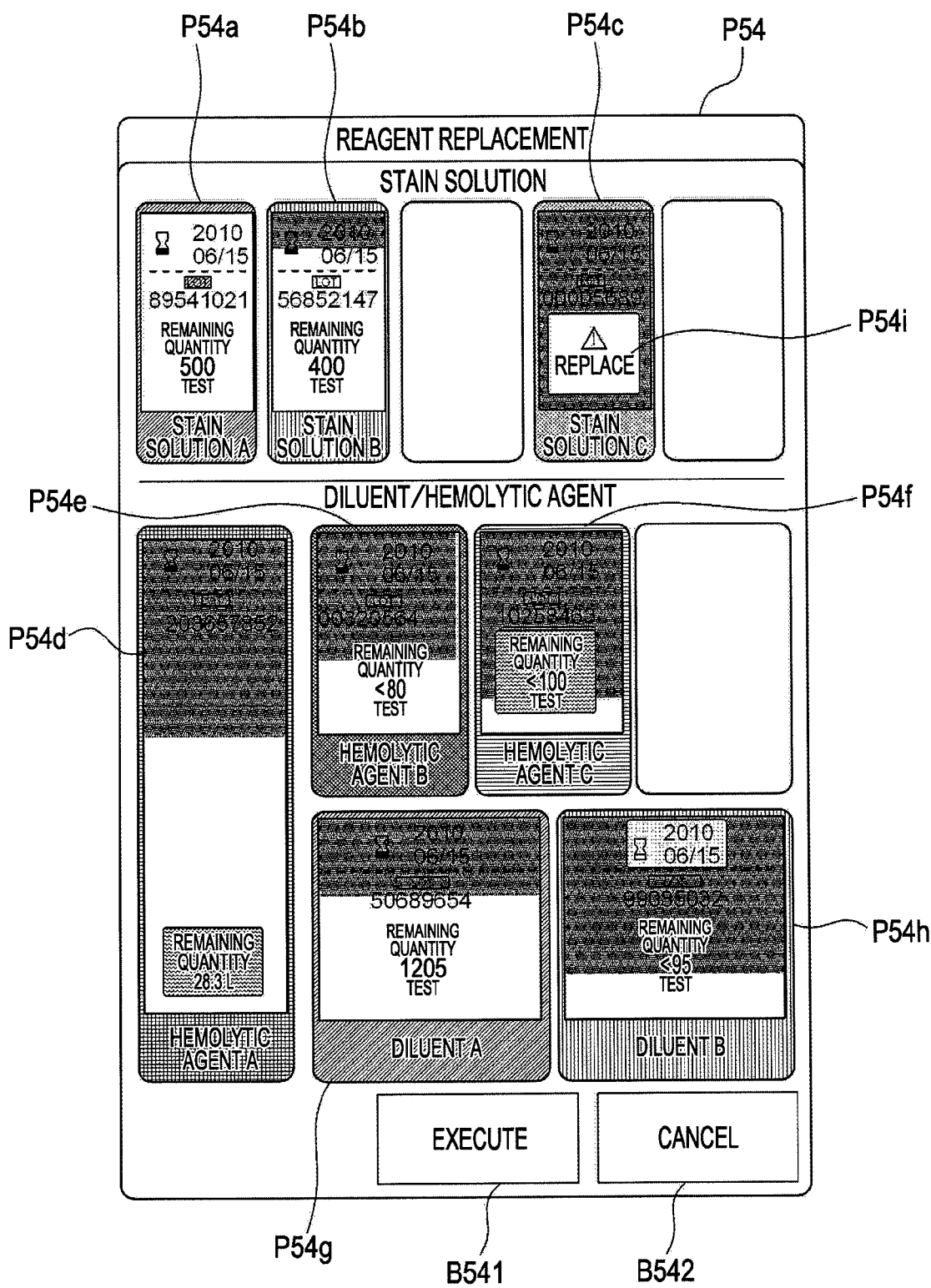
FIG. 13 is a drawing of a reagent replacement screen.

A screen display when the reagent replacement in the measurement unit 53 is requested is described in detail. As illustrated in FIG. 11, the operation menu screen P51 is displayed when the button B34 of the measurement unit operation section M3 is pressed. When the menu item P51g of the operation menu screen P51 is selected, a reagent replacement screen having a width dimension equal to that of the measurement unit operation section M3 is displayed in place of the operation menu screen P51. FIG. 13 is a drawing of the reagent replacement screen. The reagent replacement screen P54 displays thereon a plurality of icons P54a-P54h respectively provided for the reagent containers connected to the testing material preparing section 512 of the measurement unit 53. The icons P54a-P54h are displayed in the same colors as the relevant reagent containers to easily identify which of the icons and reagent container are associated with each other.

In the icons P54a-P54h, information of the respective reagents is displayed, for example, expiration date for use, lot number, number of remaining tests, reagent name. The icon of any reagent to be replaced displays thereon a warning information P541i in place of the number of remaining tests to notify that the reagent should be replaced. Any of the icons P54a-P54h is selected by the user by way of the input device 543. The icons 54a-54h are respectively displayed in the form of frame-like shapes, and there are two regions shown in different colors in the respective frames. These regions are formed by dividing the icon frame into upper and lower parts. The whole frame inside represents a storage capacity of the reagent container, while the lower region represents a remaining quantity of the reagent. More specifically, the two regions are divided at the center position in a height direction of the icon frame when the reagent remaining quantity is 50% of the whole storage capacity of the reagent container, and the two regions are divided at a position equal to 70% of the total height of the icon frame when the reagent remaining quantity is 70% of the whole storage capacity of the reagent container. When the reagent container is completely filled with the reagent, there is no division in the icon frame. Thus, the reagent remaining quantity can be roughly confirmed at a glance in each of the reagent containers.

The reagent replacement screen P54 is provided with a button B541 used to replace the reagent of the selected icon, and a button B542 used to delete the input to the reagent replacement screen P54 and make the reagent replacement screen P54 hidden. The user selects one of the icons P54a-P54h associated with the reagent to be replaced and selects the button B541 to thereby request the information processing unit 54 to replace the reagent. The CPU 541a, when the request is received, controls the measurement unit 51 to replace the reagent. More specifically, the user removes the unwanted reagent container from the measurement unit 51 and makes a reagent barcode reader, not illustrated in the drawing, provided in the measurement unit 51 read a barcode printed on the label of a new reagent container and then connects the new reagent container to the measurement unit 51. The CPU 541a requested to replace the reagent makes the reagent barcode reader read the reagent barcode to obtain information of the reagent, for example, expiration date for use, lot number, number of remaining tests, and reagent name. The CPU 541a registers the obtained reagent-related information in a reagent database, not illustrated in the drawing, provided in the hard disc 541d to update the displayed icon representing the replaced reagent based on the registered information. Then, the reagent replacement is completed.

Figure 14:
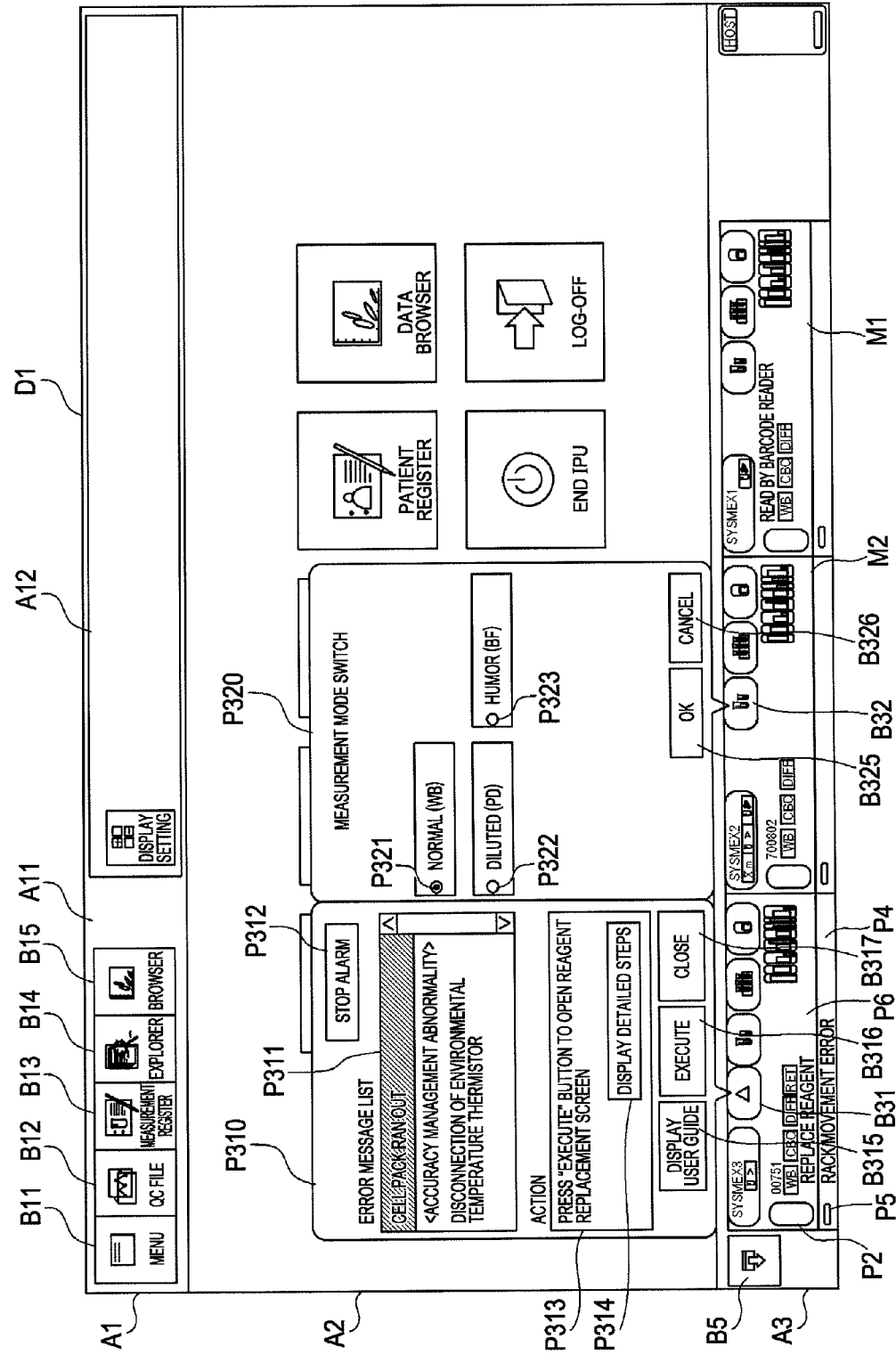
FIG. 14 is a drawing of a menu screen with an error handling screen and a measurement mode setting screen displayed thereon.

Next, a screen display when an error occurs in the measurement unit 53 is specifically described. Whenever an error occurs in the measurement unit 53, an error warning icon is displayed on the button B31 of the measurement unit operation section M3 as illustrated in FIG. 14. Further, the status notifying section P2 is displayed in red, and an error message notifying the error is displayed in the error message region P6 of the measurement unit operation section M3. When the button B31 displaying thereon the error warning icon is selected, the error handling screen is displayed immediately above the measurement unit operation section M3.

FIG. 14 is a drawing of the menu screen with the error handling screen displayed thereon. As illustrated in FIG. 14, to let the user readily know that the display of the error handling screen P310 results from selecting the button B31, the error handling screen P310 is displayed in a balloon with a triangular tip sticking out from its bottom pointing to the button B31 of the measurement unit operation M3. This helps the user to readily know which of the buttons is the origin of the error handling screen P310 currently displayed.

The error handling screen P310 is provided with an error message list region P311 which displays an error message notifying what kind of error occurred. The error message list region P311 displays a list of error messages relevant to all of the errors currently occurring in the measurement unit 53. In the example illustrated in FIG. 14, error messages displayed therein are relevant to three errors; reagent shortage, accuracy management abnormality, disconnection of environmental temperature thermistor. An error message displayed when the reagent ran out notifies which reagent specifically ran out such as "cell pack ran out". The "accuracy management abnormality" is an error of the accuracy management measurement. The "disconnection of environmental temperature thermistor" is disconnection of a thermistor provided in the measurement unit 51 as a temperature sensor. Thus, the error message list region P311 displays the error messages which notify the user what kind of error occurred.

In the example illustrated in FIG. 14, "replace reagent" is displayed in the error message region P6. In the illustrated example, an error occurred in the sample transport unit 3c during the transport of the sample rack, and "rack transport error" is displayed in the transport error display section P4 provided below the measurement unit operation section M3.

In an upper-right part of the error message list region P311, an alarm stop button P312 is displayed. The alarm stop button P312 is a selectable object (control). When the alarm stop button P312 is selected, the status notifying section P5 so far displayed in red is displayed in green, and the error message is no longer displayed in the error message region P6. Further, an alarm display and an alarm sound which started when the error occurred stop.

Below the error message list region P311, a handling method display region P313 is provided to display error handling methods. Any of the error messages displayed in the error message list region P311 is selected by the user by way of the input device 543, and a text message explaining the error handling method for the selected error message is displayed in the handling method display region P313. In the example illustrated in FIG. 14, a text message, "press [execute] button to open reagent replacement screen", is displayed in the handling method display region P313. Depending on the errors, further detailed handling methods may be presented, in which case a button P314 is displayed to show more detailed handling steps in the handling method display region P313. The button P314 is a selectively controlled button. When the button P314 is selected, a new window is displayed, in which the detailed error handling methods are displayed (not illustrated in the drawing).

Three buttons P315, P316, and P317 are provided below the handling method display region P313. These buttons P315-P317 are selectively controlled buttons. The button P315 is assigned with a function of displaying a user guide. When the button P315 is selected, user guide data (not illustrated in the drawing) stored in the hard disc 541d is read therefrom to display a user guide on the image display device 542. The user can deal with the error or confirm details of the error referring to the user guide. When a process to cancel the error indicated by the error message selected in the error message list region P311, for example, a control process for making the measurement unit execute an error canceling operation can be executed by the information processing unit, the button P316 can function to start the error canceling operation. In the example illustrated in FIG. 6, "execute" is displayed on the button P316. The button P316 is assigned with the function of displaying the reagent replacement screen. When the user selects the button P316, the reagent replacement screen can be displayed. The reagent run-out error can be cancelled when the reagent is replaced by accessing the reagent replacement screen. The button P317 is assigned with a function of disabling the display of the error handling screen P310. When the button B317 is selected, any information inputted so far to the error handling screen P310 is deleted, and the error handling screen P310 is closed.

The error handling screen P310 is displayed at a position in the main region A2 immediately above the measurement unit operation section M3 where the selected button B31 is provided. More specifically, the error handling screen P310 is displayed at a position above the measurement unit operation section M3 in a direction orthogonal to a direction where the measurement unit operation sections M1-M3 are aligned. The error handling screen P310 has a width dimension equal to that of the measurement unit operation section M3, and both ends of the error handling screen P310 are aligned with both ends of the measurement unit operation section M3.

In the example illustrated in FIG. 14, a measurement mode switch screen associated with the measurement unit operation section M2 is displayed. As illustrated in FIG. 14, when the button B32 of the measurement unit operation section M2 is selected, a measurement mode switch screen P320 is displayed immediately above the measurement unit operation section M2. To let the user readily know that the display of the measurement mode switch screen P320 results from selecting the button B32 of the measurement unit operation section M2, the measurement mode switch screen P320 is displayed in a balloon with a triangular tip sticking out from its bottom pointing to the button B32 of the measurement unit operation section M2.

The measurement mode switch screen P320 is used to set one of the measurement modes; normal sample measurement mode, diluted sample measurement mode, and humor measurement mode. The measurement mode switch screen P320 is provided with a radio button P321 used to set the normal sample measurement mode in the measurement unit 52, a radio button P322 used to set the diluted sample measurement mode therein, and a radio button P323 used to set the humor measurement mode therein. The radio buttons P321-P323 are controlled so that only one of them is selectable, meaning that two or more of the radio buttons P321-P323 cannot be selected at a time. In a lower part of the measurement mode switch screen P320, two buttons are provided; a button B325 used to set the selected measurement mode, and a button B326 used to cancel the measurement mode switch screen before setting the measurement mode. These buttons P321-P323, B325 and B326 are selectively controlled buttons. When the user presses the button B325 after the radio button P321 was selected, the measurement mode of the measurement unit 52 is set to the normal sample measurement mode. The hard disc 541d of the information processing unit 54 has a region where set values of the measurement modes of the measurement units 51-53 are stored. When the information processing unit 54 receives the inputted information, a set value of the normal sample measurement mode is stored in the region of the hard disc 541d where the set value of the measurement mode of the measurement unit 52 is stored so that the normal sample measurement mode is set in the measurement unit 52. After the button B325 is selected, the measurement mode switch screen P320 is no longer displayed. When the button B326 is pressed by the user after one of the radio buttons P321-P323 was selected, the information inputted when one of the radio buttons P321-P323 was selected is deleted, and the measurement mode switch screen P320 is no longer displayed.

The measurement mode switch screen P320 is displayed at a position in the main region A2 immediately above the measurement unit operation section M2 where the selected button B32 is provided. More specifically, the measurement mode switch screen P320 is displayed at a position above the measurement unit operation section M2 in the direction orthogonal to the direction where the measurement unit operation sections M1-M3 are aligned. Similarly to the error handling screen P310, the measurement mode switch screen P320 has a width dimension equal to that of the measurement unit operation section M2, and both ends of the measurement mode screen P31 are aligned with both ends of the measurement unit operation section M2. Because the measurement unit operation sections M3 and M2 are provided next to each other as illustrated in FIG. 14, the error handling screen P310 displayed for the measurement unit operation section M3 and the measurement mode switch screen P320 displayed for the measurement unit operation section M2 are similarly provided next to each other with no overlap therebetween. When two or more operation screens are displayed in response to the adjacent measurement unit operation sections in such a manner that the error handling screen P310 and the measurement mode switch screen P320 are displayed in FIG. 14, there is no overlap between the two operation screens, helping the user to easily handle the operation screens.

As described so far, in the sample processing system 1 according to the present exemplary embodiment, the main region A2 and the operation region A3 including the three measurement unit operation sections M1-M3 respectively used to operate the measurement units 51-53 are provided on the display screen of the information processing unit 54. Therefore, the user can operate the measurement units 51-53 while displaying such screens as the measurement result detail screen and the measurement order register screen in the main region A2. This facilitates the operation of the measurement unit 51 by the user.

According to the present exemplary embodiment, the measurement unit operation sections M1-M3 are continuously displayed after the display of the main region A2 is switched. Therefore, the user can instantly access the measurement unit operation sections M1-M3 to input thereto the operation instructions or settings of the measurement units 51-53. This facilitates the operation of the measurement unit 51 by the user.

Another Exemplary Embodiment

Figure 15:
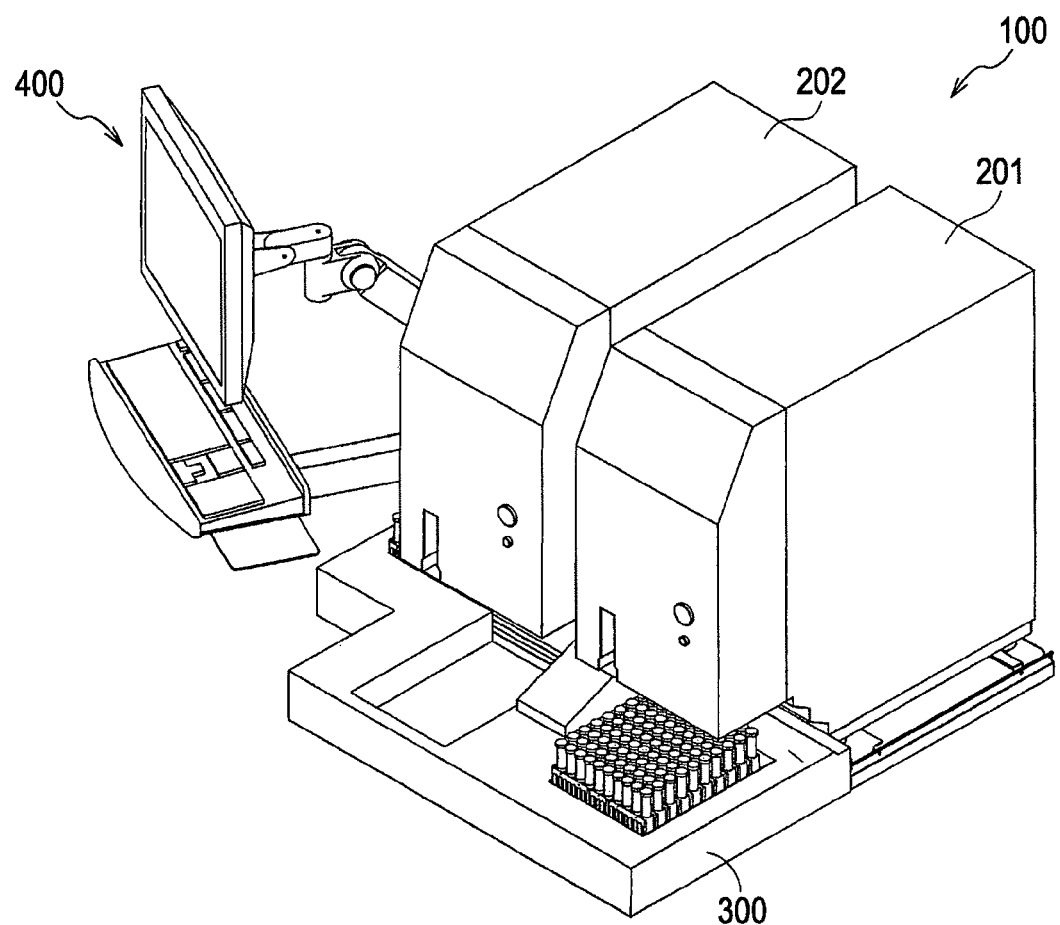
FIG. 15 is a perspective view illustrating a structure of a blood cell analysis apparatus according to another embodiment of the present invention.

The exemplary embodiment described the display screens of the information processing unit 54 in the sample processing system 1 provided with the blood cell analysis apparatus 5 and the smear sample production apparatus 6, however, the present invention is not necessarily limited thereto. FIG. 15 is a perspective view illustrating a structure of a blood cell analysis apparatus according to another exemplary embodiment of the present invention. As illustrated in the drawing, a blood cell analysis apparatus 100 includes two measurement units 201 and 202, a sample transport unit 300, and an information processing unit 400. The screens described so far may be similarly displayed on a screen of the information processing unit 400.

According to the exemplary embodiment described so far, the buttons B31, B32, B33, and B34 are provided in the measurement unit operation sections M1, M2, and M3 as objects used to manipulate the measurement units. Other examples of the objects that may be provided in the measurement unit operation sections M1, M2, and M3 are icons, and menu buttons to display pull-down menus or pop-up menus.

According to the exemplary embodiment described so far, the icons are displayed as objects to be displayed in the main region A2 of the menu screen D1. Other examples of the objects that may be displayed in the main region A2 are buttons, or menu buttons to display pull-down menus.

According to the exemplary embodiment described so far, the sample numbers, measurement dates and times, and measurement order receiving dates and time are displayed as a list of information to be displayed in the main region A2 as illustrated in FIG. 7. The list of information to be displayed in the main region A2 may be patient-related information such as patient IDs, patient names, and attending doctors.

According to the exemplary embodiment described so far, the sample measurement result obtained by one of the measurement units is displayed in the main region A2 as illustrated in FIG. 9. In place of the measurement result or alongside the measurement result, patient disorder information of a patient which provided the relevant sample (for example, disorder possibly affecting patient, measurement result unique to the disorder, literatures relating to the disorder) may be displayed in the main region A2.

The measurement units 51, 52, and 53 may be configured to directly suction the samples from the sample containers held in the sample rack on the measurement line 3M.

According to the exemplary embodiment described so far, the measurement units 51 and 52 are capable of the sample measurement for CBC and DIFF but not for RET, and the measurement unit 53 is capable of the sample measurement for CBC, DIFF, and RET. However, the present invention is not necessarily limited thereto. All of the measurement units 51, 52, and 53 may be configured to equally measure the samples for the same measurement items (CBC, DIFF, RET).

According to the exemplary embodiment described so far, when the buttons B31-B34 of the measurement unit operation sections M1-M3 are pressed, the operation screens responding to the pressed buttons B31-B34 are displayed in such a manner that the content displayed in the main region A2 is hidden in the upper parts of the measurement unit operation sections M1-M3. However, the present invention is not necessarily limited thereto. The operation screen to be displayed may be semi-translucent so that the content of the main region A2 behind the operation screen can be seen through the operation screen.

The exemplary embodiment described the display screens of the information processing unit 54 in the blood cell analysis apparatus 5, however, the present invention is not necessarily limited thereto. Any other sample processing apparatuses having a plurality of sample processing units, for example; blood coagulation measuring apparatus, smear sample production apparatus, urine cell analyzer, biochemical analyzer, and immunity analyzer, may display a screen having a plurality of sample processing unit operation sections respectively used to manipulate the sample processing units apart from a main region where contents including sample processing results are displayed.

The exemplary embodiment described the blood cell analysis apparatus 5 provided with the three measurement units 51, 52, and 53, and one information processing unit 54, however, the present invention is not necessarily limited thereto. There may be more or less measurement units than three. In place of using the information processing unit 54 to control the mechanisms of the measurement units 51, 52, and 53, each of the measurement units is provided with a controller including a CPU and a memory, wherein the information processing unit 54 inputs the operation instructions of the measurement units 51-53 to the controllers so that the respective controllers are responsible for operating the measurement units.

What is claimed is:
1. A sample processing apparatus, comprising:
   a first sample processing unit configured to process a sample;
   a second sample processing unit configured to process a sample; and
   a data processing unit connected to the first and the second sample processing units to communicate therewith, wherein
   the data processing unit includes:
      a display device;
      an input device; and
      a controller configured to show a screen image on the display device,
   wherein the screen image comprises:
      a shared region which is shared for displaying information of each of the first and the second sample processing units;
      a first operation section operable through the input device by a user to control the first sample processing unit, wherein the first operation section comprises first objects; and
      a second operation section operable through the input device by the user to control the second sample processing unit, wherein the second operation section comprises second objects,
   wherein the controller is configured to display a first processing start screen image which overlaps the information displayed in the shared region in response to an operation of one of the first objects, and display a second processing start screen image which overlaps the information displayed in the shared region in response to an operation of one of the second objects, and
   wherein the controller is configured to control the first sample processing unit in response to an operation of the first operation section by the user, and control the second sample processing unit in response to an operation of the second operation section by the user, wherein the controller is configured to control the first sample processing unit to start a sample process in response to an operation of the first processing start screen image by the user, and control the second sample processing unit to start a sample process in response to an operation of the second processing start screen image by the user.

2. The sample processing apparatus according to claim 1, wherein the controller is configured to switch a display of the shared region independently from the first and the second operation sections.

3. The sample processing apparatus according to claim 1, wherein
the controller is configured to display, in the shared region at a time, information of a sample processed by the first sample processing unit and information of another sample processed by the second processing unit.

4. The sample processing apparatus according to claim 3, wherein
the controller is configured to display, in the shared region, a list of identification information and processing dates and times of samples processed by the first and the second sample processing units.

5. The sample processing apparatus according to claim 1, wherein
the controller is configured to display information of a first sample processed by the first sample processing unit in the shared region and then switch a display of the shared region from the information of the first sample to information of a second sample processed by the second sample processing unit.

6. The sample processing apparatus according to claim 5, wherein
the controller is configured to display information indicating a processing result of the first sample by the first sample processing unit in the shared region as the information of the first sample, and display information indicating a processing result of the second sample by the second sample processing unit in the shared region as the information of the second sample.

7. The sample processing apparatus according to claim 1, wherein
the controller is configured to display the first operation screen image at a position adjacent to the first object, and display the second operation screen image at a position adjacent to the second object.

8. The sample processing apparatus according to claim 7, wherein
each of the first and the second operation screen images has a display area smaller than that of the shared region.

9. The sample processing apparatus according to claim 1, wherein the controller is configured to display at least one of an error handling screen image for handling an error generated in the first sample processing unit, a control mode setting screen image for setting an control mode of the first sample processing unit, and the controller is configured to display at least one of an error handling screen image for handling an error generated in the second sample processing unit, and a control mode setting screen image for setting an control mode of the second sample processing unit.

10. The sample processing apparatus according to claim 1, wherein the controller is configured to display the first and the second processing start screen images at a time.

11. The sample processing apparatus according to claim 10, wherein the controller is configured to display an object operable by the user to hide the first and the second processing start screen images, and hide the first and the second processing start screen images currently displayed in response to an operation of the object.

12. The sample processing apparatus according to claim 1, wherein
the controller is configured to display, in an upper end of the screen image, a tool bar region including a plurality of objects selectable by the user to switch a display of the shared region, display, in a lower end of the screen image, an operation region including the first and the second operation sections, and display the shared region between the tool bar region and the operation region.

13. The sample processing apparatus according to claim 1, wherein
the controller is configured to display first status information indicating status of the first sample processing unit on the first operation section and display second status information indicating status of the second sample processing unit on the second operation section.

14. The sample processing apparatus according to claim 13, wherein
the controller is configured to display, on the first operation section as the first status information, at least one of: error information indicating that an error is generated in the first sample processing unit; reagent remaining quantity information indicating a remaining quantity of a reagent used to process a sample in the first sample processing unit; sample identifying information used to identify a sample to be processed by the first sample processing unit; operation mode information indicating an operation mode set in the first sample processing unit; and processing item information indicating a processing item for which a sample is processed in the first sample processing unit, and
the controller is configured to display, on the second operation section as the second status information, at least one of: error information indicating that an error is generated in the second sample processing unit; reagent remaining quantity information indicating a remaining quantity of a reagent used to process a sample in the second sample processing unit; sample identifying information used to identify a sample to be processed by the second sample processing unit; operation mode information indicating an operation mode set in the second sample processing unit; and processing item information indicating a processing item for which a sample is processed in the second sample processing unit.

15. The sample processing apparatus according to claim 1, wherein
each of the first and the second sample processing units is configured to measure a sample for a plurality of measurement items, and at least a part of the measurement items are common between the first and the second sample processing units.

16. The sample processing apparatus according to claim 1, further comprising
a third sample processing unit configured to process a sample, wherein
the screen image comprises a third operation section operable by the user to control the third sample processing unit.

17. At least one non-transitory storage medium which stores programs executable collectively by at least one processor to:
show a screen image on a display device, wherein the screen image comprises:
a shared region which is shared for displaying information of each of a first sample processing unit and a second sample processing unit, a first operation section operable by a user to control the first sample processing unit, wherein the first operation section comprises first objects; and
a second operation section operable by the user to control the second sample processing unit, wherein the second operation section comprises second objects;

wherein the controller is configured to display a first processing start screen image which overlaps the information displayed in the shared region in response to an operation of one of the first objects and display a second processing start screen image which overlaps the information displayed in the shared region in response to an operation of one of the second objects, and wherein the controller is configured to control the first sample processing unit in response to an operation of the first operation section, and control the second sample processing unit in response to an operation of the second operation section, wherein the controller is configured to control the first sample processing unit to start a sample process in response to an operation of the first processing start screen image by the user, and control the second sample processing unit to start a sample process in response to an operation of the second processing start screen image by the user.

18. The non-transitory storage medium of claim 17, wherein the processor is programmed to switch a display of the shared region independently from the first and the second operation sections.

* * * * *